US008962278B2

(12) United States Patent
Yusibov et al.

(10) Patent No.: US 8,962,278 B2
(45) Date of Patent: Feb. 24, 2015

(54) COMPOSITIONS AND METHODS FOR PRODUCTION OF IMMUNOGLOBULINS

(75) Inventors: Vidadi Yusibov, Havertown, PA (US); Vadim Mett, Newark, DE (US); Anna Hull, West Grove, PA (US)

(73) Assignee: iBio Inc., Newark, DE (US)

( * ) Notice: Subject to any disclaimer, the term of this patent is extended or adjusted under 35 U.S.C. 154(b) by 2577 days.

(21) Appl. No.: 11/498,522

(22) Filed: Aug. 3, 2006

(65) Prior Publication Data

US 2010/0239594 A1     Sep. 23, 2010

Related U.S. Application Data

(60) Provisional application No. 60/705,653, filed on Aug. 3, 2005.

(51) Int. Cl.

| A61K 39/40 | (2006.01) |
|---|---|
| C12P 21/02 | (2006.01) |
| C12P 19/34 | (2006.01) |
| C12N 5/10 | (2006.01) |
| C12N 15/83 | (2006.01) |
| C07K 16/12 | (2006.01) |
| C07H 21/04 | (2006.01) |
| A61P 31/04 | (2006.01) |
| A01H 5/00 | (2006.01) |
| A01K 67/00 | (2006.01) |
| A61K 39/00 | (2006.01) |

(52) U.S. Cl.
CPC ....... *C07K 16/1278* (2013.01); *A61K 2039/505* (2013.01); *C07K 2317/13* (2013.01); *C07K 2317/21* (2013.01); *C07K 2317/565* (2013.01)
USPC ...... 435/91.2; 435/69.6; 435/320.1; 435/419; 424/164.1; 536/23.53; 536/24.33; 530/387.3; 530/389.5

(58) Field of Classification Search
None
See application file for complete search history.

(56) References Cited

U.S. PATENT DOCUMENTS

| 4,196,265 A | 4/1980 | Koprowski et al. |
|---|---|---|
| 4,270,537 A | 6/1981 | Romaine |
| 4,522,811 A | 6/1985 | Eppstein et al. |
| 4,596,556 A | 6/1986 | Morrow et al. |
| 4,653,728 A | 3/1987 | Mochizuki et al. |
| 4,683,202 A | 7/1987 | Mullis |
| 4,790,824 A | 12/1988 | Morrow et al. |
| 4,816,567 A | 3/1989 | Cabilly |
| 4,886,499 A | 12/1989 | Cirelli et al. |
| 4,935,496 A | 6/1990 | Kudo et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,223,409 A | 6/1993 | Ladner et al. |
| 5,312,335 A | 5/1994 | McKinnon et al. |
| 5,316,931 A | 5/1994 | Donson et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,403,484 A | 4/1995 | Ladner et al. |
| 5,417,662 A | 5/1995 | Hjertman et al. |
| 5,427,908 A | 6/1995 | Dower et al. |
| 5,466,220 A | 11/1995 | Brenneman |
| 5,480,381 A | 1/1996 | Weston |
| 5,500,360 A | 3/1996 | Ahlquist et al. |
| 5,502,167 A | 3/1996 | Waldmann et al. |
| 5,503,627 A | 4/1996 | McKinnon et al. |
| 5,520,639 A | 5/1996 | Peterson et al. |
| 5,527,288 A | 6/1996 | Gross et al. |
| 5,530,101 A | 6/1996 | Queen et al. |
| 5,545,806 A | 8/1996 | Lonberg et al. |

(Continued)

FOREIGN PATENT DOCUMENTS

| EP | 404097 | 6/1990 |
|---|---|---|
| WO | WO 9302108 A1 * | 2/1993 |

(Continued)

OTHER PUBLICATIONS

Bowie et al (Science, 1990, 257:1306-1310).*
Bork (Genome Research, 2000,10:398-400).*
Davies et al., "Affinity improvement of single antibody VH domains: residues in all three hypervariable regions affect antigen binding", *Immunotechnology*, Elsevier Science Publishers BV, NL, vol. 2, No. 3, Sep. 1996, pp. 169-179.
Holt et al., "Domain antibodies: proteins for therapy", *Trends in Biotechnology*, Elsevier Publications, Cambridge, GB, vol. 21, No. 11, Nov. 2003, pp. 484-490.

(Continued)

*Primary Examiner* — Robert A Zeman
(74) *Attorney, Agent, or Firm* — Fish & Richardson P.C.

(57) ABSTRACT

Provided are oligonucleotides for isolating human antibody cDNAs from cells or cell lines, such as hybridomas. The invention also provides cDNAs that encode at least one provided CDR of a heavy chain or a light chain of a human monoclonal antibody that binds to *B. anthracis* protective antigen; and cDNAs that encode at least one provided CDR of a heavy chain or a light chain of a human monoclonal antibody that binds to *B. anthracis* lethal factor. The invention further provides expression vectors that contain one or more cDNAs isolated according to the methods of the invention, host cells expressing one or more inventive cDNAs, and transgenic plants and animals that express one or more inventive cDNAs. In certain embodiments of the invention the expression system is a plant-based expression system. The invention further provides antibody compositions comprising one or more antibodies produced by expressing a cDNA isolated according to the methods of the invention in a suitable expression system. Additionally encompassed in the invention are kits containing one or more of provided compositions, as well as methods of production and use of provided compositions.

5 Claims, 2 Drawing Sheets

(56) References Cited

U.S. PATENT DOCUMENTS

| | | |
|---|---|---|
| 5,545,807 A | 8/1996 | Surani et al. |
| 5,558,864 A | 9/1996 | Bendig et al. |
| 5,565,332 A | 10/1996 | Hoogenboom et al. |
| 5,569,189 A | 10/1996 | Parsons |
| 5,569,825 A | 10/1996 | Lonberg et al. |
| 5,580,717 A | 12/1996 | Dower et al. |
| 5,585,089 A | 12/1996 | Queen et al. |
| 5,591,828 A | 1/1997 | Bosslet et al. |
| 5,599,302 A | 2/1997 | Lilley et al. |
| 5,602,242 A | 2/1997 | Ahlquist et al. |
| 5,625,126 A | 4/1997 | Lonberg et al. |
| 5,633,425 A | 5/1997 | Lonberg et al. |
| 5,639,641 A | 6/1997 | Pedersen et al. |
| 5,649,912 A | 7/1997 | Peterson |
| 5,658,727 A | 8/1997 | Barbas et al. |
| 5,661,016 A | 8/1997 | Lonberg et al. |
| 5,667,988 A | 9/1997 | Barbas et al. |
| 5,681,722 A | 10/1997 | Newman et al. |
| 5,693,493 A | 12/1997 | Robinson et al. |
| 5,693,761 A | 12/1997 | Queen et al. |
| 5,693,762 A | 12/1997 | Queen et al. |
| 5,698,417 A | 12/1997 | Robinson et al. |
| 5,698,426 A | 12/1997 | Huse et al. |
| 5,702,892 A | 12/1997 | Mulligan-Kehoe |
| 5,704,911 A | 1/1998 | Parsons |
| 5,705,154 A | 1/1998 | Dalie et al. |
| 5,733,743 A | 3/1998 | Johnson et al. |
| 5,750,078 A | 5/1998 | Shitara et al. |
| 5,759,817 A | 6/1998 | Barbas |
| 5,770,403 A | 6/1998 | Dalie et al. |
| 5,770,429 A | 6/1998 | Lonberg et al. |
| 5,846,795 A | 12/1998 | Ahlquist et al. |
| 5,855,866 A | 1/1999 | Thorpe et al. |
| 5,877,289 A | 3/1999 | Thorpe et al. |
| 5,888,789 A | 3/1999 | Rodriguez et al. |
| 5,893,397 A | 4/1999 | Peterson et al. |
| 5,959,085 A * | 9/1999 | Garrone et al. ............ 530/387.3 |
| 5,965,132 A | 10/1999 | Thorpe et al. |
| 5,993,412 A | 11/1999 | Deily et al. |
| 6,004,555 A | 12/1999 | Thorpe et al. |
| 6,042,832 A | 3/2000 | Koprowski et al. |
| 6,093,399 A | 7/2000 | Thorpe et al. |
| 6,103,511 A | 8/2000 | Li et al. |
| 6,261,535 B1 | 7/2001 | Thorpe et al. |
| 6,331,415 B1 | 12/2001 | Cabilly et al. |
| 6,448,070 B1 | 9/2002 | Koprowski et al. |
| 6,524,825 B1 | 2/2003 | Mizzen et al. |
| 6,649,172 B2 | 11/2003 | Johnson |
| 6,734,173 B1 | 5/2004 | Wu et al. |
| 6,740,740 B2 | 5/2004 | Garger et al. |
| 6,797,491 B2 | 9/2004 | Neefe, Jr. et al. |
| 6,841,659 B2 | 1/2005 | Turpen et al. |
| 6,852,319 B2 | 2/2005 | Hein et al. |
| 7,658,925 B2 * | 2/2010 | Groen et al. ............... 424/164.1 |
| 7,888,135 B2 | 2/2011 | Tarleton et al. |
| 2004/0092470 A1 | 5/2004 | Leonard et al. |
| 2004/0093643 A1 | 5/2004 | Ensley |
| 2004/0170606 A1 | 9/2004 | Palmer et al. |
| 2004/0268442 A1 | 12/2004 | Miller et al. |
| 2005/0026291 A1 | 2/2005 | Fedorkin et al. |
| 2005/0042229 A1 | 2/2005 | Yang et al. |
| 2005/0048074 A1 | 3/2005 | Cardineau et al. |
| 2005/0054820 A1 | 3/2005 | Wu et al. |
| 2005/0114920 A1 | 5/2005 | Yusibov et al. |
| 2005/0186621 A1 | 8/2005 | Galarza et al. |
| 2006/0008473 A1 | 1/2006 | Yang et al. |
| 2006/0265787 A1 | 11/2006 | Piruzian et al. |
| 2007/0275014 A1 | 11/2007 | Yusibov et al. |
| 2008/0124272 A1 | 5/2008 | Yusibov et al. |
| 2008/0279877 A1 | 11/2008 | Yusibov et al. |
| 2009/0324634 A1 | 12/2009 | Knapp et al. |
| 2010/0227373 A1 | 9/2010 | Yusibov et al. |
| 2011/0027304 A1 | 2/2011 | Yusibov et al. |
| 2011/0059130 A1 | 3/2011 | Yusibov |

FOREIGN PATENT DOCUMENTS

| | | |
|---|---|---|
| WO | WO9311161 | 6/1993 |
| WO | WO 9514780 A2 * | 6/1995 |
| WO | WO9602555 | 2/1996 |
| WO | WO9612028 | 4/1996 |
| WO | WO 9636358 A1 * | 11/1996 |
| WO | WO9713537 | 4/1997 |
| WO | WO9737705 | 10/1997 |
| WO | WO9814595 | 4/1998 |
| WO | WO9845331 | 10/1998 |
| WO | WO9907860 | 2/1999 |
| WO | WO0020612 | 4/2000 |
| WO | WO0025574 | 5/2000 |
| WO | WO0046350 | 8/2000 |
| WO | WO0200892 | 1/2002 |
| WO | WO03040179 | 5/2003 |
| WO | WO03057834 | 7/2003 |
| WO | WO03076568 | 9/2003 |
| WO | WO2004043886 | 5/2004 |
| WO | WO2004058797 | 7/2004 |
| WO | WO2005023177 | 3/2005 |
| WO | WO2005026375 | 3/2005 |
| WO | WO2005049839 | 6/2005 |
| WO | WO2005056052 | 6/2005 |
| WO | WO2005067620 | 7/2005 |
| WO | WO2005081905 | 9/2005 |
| WO | WO2005120567 | 12/2005 |
| WO | WO2006003018 | 1/2006 |
| WO | WO2006124712 | 11/2006 |
| WO | WO2007089753 | 8/2007 |
| WO | WO2007095304 | 8/2007 |
| WO | WO2007095318 | 8/2007 |
| WO | WO2007117264 | 10/2007 |
| WO | WO2007149715 | 12/2007 |
| WO | WO2008021959 | 2/2008 |
| WO | WO2008033105 | 3/2008 |
| WO | WO2008033159 | 3/2008 |
| WO | WO2008048945 | 4/2008 |
| WO | WO2008110937 | 9/2008 |
| WO | WO2008134643 | 11/2008 |
| WO | WO2009009759 | 1/2009 |
| WO | WO2009026397 | 2/2009 |
| WO | WO2009054708 | 4/2009 |
| WO | WO2009058355 | 5/2009 |
| WO | WO2010036970 | 4/2010 |
| WO | WO2010037046 | 4/2010 |

OTHER PUBLICATIONS

Hull et al., "Human-derived, plant-produced monoclonal antibody for the treatment of anthrax", *Vaccine*, Butterworth Scientific, Guildford, GB, vol. 23, No. 17-18, Mar. 18, 2005, pp. 2082-2086.

Little et al., "Of mice and men: hybridoma and recombinant antibodies", *Immunology Today*, Elsevier Publications, Cambridge, GB, vol. 21, No. 8, Aug. 1, 2000, pp. 364-370.

Communication dated May 19, 2009 for European Application No. 06850507.2.

International Search Report and Written Opinion dated Apr. 4, 2008 for International Application No. PCT/US2006/030545.

International Preliminary Report on Patentability dated Apr. 23, 2008 for International Application No. PCT/US2006/030545.

Accession CAA4959, Apr. 18, 2005.

Ahlquist et al., "Gene Expression Vectors Derived from Plant RNA Viruses," *Current Communications in Molecular Biology—Viral Vectors*, (Ed., Gluzman et al.) pp. 183-189, 1988.

Akol and Murray, "Trypanosoma congolense: Susceptibility of cattle to cyclical challenge," *Exp. Parasitol.*, 55:386-393, 1983.

Alignment of 11706573-6 to SEQ ID No. 6 cited in parent U.S. Appl. No. 10/558,109 on Feb. 24, 2009.

Alignment of 11706573-30 to SEQ ID No. 6 cited in parent U.S. Appl. No. 10/558,109 on Feb. 24, 2009.

Alignment of 11706576-12 to SEQ ID No. 6 cited in parent U.S. Appl. No. 10/558,109 on Feb. 24, 2009.

Alignment of 12110877-30 to SEQ ID No. 6 cited in parent U.S. Appl. No. 10/558,109 on Feb. 24, 2009.

(56) References Cited

OTHER PUBLICATIONS

Altschul et al., "Basic local alignment search tool," *J. Mol. Biol.* 215:403-410, 1990.
Altschul et al., "Gapped BLAST and PSI-BLAST: a new generation of protein database search programs," *Nucleic Acids Res.* 25: 3389-3402, 1997.
Alvarez et al., "Plant-made subunit vaccine against pneumonic and bubonic plague is orally immunogenic in mice," *Vaccine* 24(14): 2477-2490, 2006.
Anderson et al., "Recombinant V Antigen Protects Mice against Pneumonic and Bubonic Plague Caused by F1-Capsule-Positive and -Negative Strains of *Yersinia pestis*," *Infect. Immun.* 64(11): 4580-5, 1996.
Andrews et al., "Fraction 1 Capsular Antigen (F1) Purification from *Yersinia pestis* CO92 and from an *Escherichia coli* Recombinant Strain and Efficacy against Lethal Plague Challenge," *Infect. Immun.* 64(6): 2180-7, 1996.
Ay et al., "Crystal structures and properties of de novo circularly permuted 1,3-1,4-beta-glucanases," *Proteins* 30(2): 155-67, 1998.
Barfield et al., "Gene Transfer in Plants of *Brassica juncea* Using *Agrobacterium tumefaciens* Mediated Transformation," *Plant Cell Reports* 10(6/7): 308-14, 1991.
Bates, "Genetic Transformation of Plants by Protoplast Electroporation," *Molecular Biotechnol.,* 2(2):135-145, 1994.
Beachy et al., "A Genetic Map for the Cowpea Strain of TMV" *Virology* 73: 498-507, 1976.
Bedell et al., "The E6-E7 Region of Human Papillomavirus Type 18 is Sufficient for Transformation of NIH 3T3 and Rat-1 Cells," *J. Virol.* 61:3635-40, 1987.
Bisaro et al., "Genetic Analysis of Tomato Golden Mosaic Virsu," *Current Communications in Molecular Biology: Viral Vectors*, Cold Spring Harbor Laboratory, Cold Spring Harbor, NY, pp. 172-189, 1988.
Bol et al., "A Functional Equivalence of Top Component A RNA and Coat Protein in the Initiation of Infection by Alfalfa Mosaic Virus" *Virology* 46: 73-85, 1971.
Bol et al., "Alfalfa Mosaic Virus and Ilarviruses: Involvement of Coat Protein in Multiple Steps of the Replication Cycle" *J.. Gen. Virol.* 80: 1089-1102, 1999.
Boyd and Beeson, "Animal models for evaluation of compounds against influenza viruses," *J. Antimicrobial Chemother.* 1 (*Suppl.*): 43-47, 1975.
Brett et al., "Immunization against influenza A virus: comparison of conventional inactivated, live-attenuated and recombinant baculovirus produced purified hemagglutinin and neuraminidase vaccines in a murine model system," *Virology* 339(2): 273-280, 2005.
Broothaerts et al., "Gene transfer to plants by diverse species of bacteria," *Nature* 433:629-33, 2005.
Brodzik et al., "Advances in alfalfa mosaic virus-mediated expression of anthrax antigen in planta," Biochem. *Biophys. Res. Commun.* 338(2): 717-722, 2005.
Bruening et al. "In Vitro and In Vivo Translation of the Ribonucleic Acids of a Cowpea Strain of Tobacco Mosaic Virus," *Virology* 71: 498-517, 1976.
Buscaglia et al., "Tandem amino acid repeats from *Trypanosoma* cruzi shed antigens increase the half-life of proteins in blood," *Blood* 93(6): 2025-2032, 1999.
Calandrelli et al., "Purification and characterization of thermostable eylanase and beta-xylosidase by the termophilic bacterium *Bacillus* termantarcticus," *Res. Microbiol.* 155(4): 283-9, 2004.
Canizares et al., "Use of viral vectors for vaccine production in plants," *Immunol. Cell Biol.* 83:263-270, 2005.
Chain et al., "Complete Genome Sequence of *Yersinia pestis* Strains Antigua and Nepal516: Evidence of Gene Reduction in an Emerging Pathogen," *J. Bacteriol.* 188(12): 4453-63, 2006.
Chen et al., "Complete sequence of the binary vector pB1121 and its application in cloning T-DNA insertion from transgenic plants," *Mol. Breed.*, 11: 287-293, 2003.
Chen et al., "Induction and relief of nasal congestion in ferrets infected with influenza virus," *Int. J. Exp. Path.* 76: 55-64, 1995.
Chica et al., "Semi-rational approaches to engineering enzyme activity: combining the benefits of directed evolution and rational design," *Curr. Opin. Biotechnol.* 16:378-384, 2005.
Chichester et al., "Different response requirements for IFNγ production in ELISPOT assays by CD4+ T cells from mice early and late after submission," *J. Immunol. Methods* 309: 99-107, 2006.
Chichester et al., "Immunogenicity of a subunit vaccine against *Bacillus anthracis," Vaccine* 25:3111-3114, 2007.
Corbel, "Reasons for instability of bacterial vaccines," *Developments in Biological Standardization*, 87: 113-124, 1996.
Costa et al., "Conformational stability and antibody response to the 18kDa heat-shock protein formulated into different vehicles," *Appl. Biochem. Biotechnol.* 73(1): 19-28, 1998.
Crossway et al., "Integration of foreign DNA following microinjection of tobacco mesophyll protoplasts," *Mol. Gen. Genet.* 202:179-185, 1986.
Curtis and Nam, "Transgenic radish (*Raphanus sativus* L. *longipinnatus* Bailey) by floral-dip method—plant development and surfactant are important in optimizing transformation efficiency," *Transgenic Research* 10(4):363-371, 2001.
DeGraff et al., "In Vitro Evidence that the Coat Protein of Alfalfa Mosaic Virus Plays a Direct Role in the Regulation of Plus and Minus RNA Synthesis Implications for the Life Cycle of Alfalfa Mosaic Virus," *Virology* 208: 583-589, 1995.
Deng et al., "Genome Sequence of *Yersinia pestis* KIM," *J. Bacteriol.* 184(16):4601-11, 2002.
Desfeux et al., "Female Reproductive Tissues Are the Primary Target of *Agrobacterium*-Mediated Transformation by the Arabidopsis Floral-Dip Method," *Plant Physiology* 123(3):895-904, 2000.
Dréau et al., "Human Papilloma Virus in Melanoma Biopsy Specimens and Its Relation to Melanoma Progression," *Annals of Surgery* 231:664-671, 2000.
Eckert et al., *PCR Methods and Applications*, 1:17, 1991.
Fenton et al., "Immunity to Influenza in Ferrets. XIV: Comparative Immunity Following Infection or Immunization with Live or Inactivated Vaccine," *Br. J. Exp. Path.* 62: 297, 1981.
Fernando et al., "Expression, purification and immunological characterization of the transforming protein E7, from cervical cancer-associated human papillomavirus type 16," *Clin Exp Immunol* 115:397-403, 1999.
Flick-Smith et al., "A Recombinant Carboxy-Terminal Domain of the Protective Antigen of *Bacillus anthracis* Protects Mice against Anthrax Infection," *Infect. Immun.* 70:1653-1656, 2002.
Fraley et al., "Liposome-Mediated Delivery of Tobacco Mosaic Virus RNA Into Tobacco Protoplasts: A Sensitive Assay for Monitoring Liposome-Protoplast Interactions," *Proc. Natl. Acad. Sci. USA* 79: 1859-1863, 1982.
Fraley et al., "Expression of Bacterial Genes in Plant Cells," *Proc. Natl. Acad. Sci. USA* 80: 4803-4807, 1983.
Franconi et al., "Plant-derived Human Papillomavirus 16 E7 Oncoprotein Induces Immune Response and Specific Tumor Production," *Cancer Res.* 62:3654, 2002.
Fromm et al., "Expression of Genes Transferred Into Monocot and Dicot Plant Cells by Electroporation," *Proc. Natl. Acad. Sci. USA* 82: 5824, 1985.
Fütterer et al., "Use of DNA Plant Viruses and Plant Viral Expression Signals for Gene Expression in Plants and Plant Protoplasts," *Current Communications in Molecular Biology—Viral Vectors*, (Ed., Gluzman et al.) pp. 178-182, 1988.
Gelvin, "*Agrobacterium*-Mediated Plant Transformation: the Biology behind the 'Gene-Jockeying' Tool," *Microbiol. Mol Biol. Rev.* 67(1):16-37, 2003.
Giri and Narasu, "Transgenic hairy roots: recent trends and applications," *Biotechnol. Adv.* 18:1-22, 2000.
Gleba et al., "Magnifection—a new platform for expressing recombinant vaccines in plants," *Vaccine* 23:2042-2048, 2005.
Goldenkova et al., "A Thermostable *Clostridium thermocellum* Lichenase-based Reporter System for Studying the Gene Expression Regulation in Prokaryotic and Eukaryotic Cells," *Mol. Biol.* 36:698-704, 2002.
Green et al., "Transient protein expression in three Pisum sativum (green pea) varieties," *Biotechnol. J.* 4(2): 230-237, 2009.

(56) References Cited

OTHER PUBLICATIONS

Grierson et al., "Plant Viruses," *Plant Molecular Biology*, Blackie, London, pp. 126-146, 1984.
Gu et al., "Protection against anthrax toxin by vaccination with a DNA plasmid encoding anthrax protective antigen," *Vaccine* 17:340, 1999.
Hahn et al., "Native-like in-vivo folding of a circularly permuted jellyroll protein shown by crystal structure analysis," *Proc. Natl. Acad. Sci. USA* 91(22):10417-10421, 1994.
Hansen et al., "Attachment of antibodies to sterically stabilized liposomes: evaluation, comparison and optimization of coupling procedures," *Biochim Biophys Acta.* 1239(2):133-44, 1995.
Heath et al., "Protection against experimental bubonic and pneumonic plague by a recombinant capsular F1-V antigen fusion protein vaccine," *Vaccine* 16(11/12):1131-7, 1998.
Hellens et al., "pGreen: a versatile and flexible binary Ti vector for *Agrobacterium*-mediated plant transformation," *Plant Mol. Biol.* 42: 819-832, 2000.
Herbert and Lumsden, "*Trypanosoma brucei*: A rapid 'matching' method for estimating the host's parasitemia," Exp. Parasitol, 40:427, 1976.
Hobson et al., "The role of serum haemagglutination-inhibiting antibody in protection against challenge infection with influenza A2 and B viruses," *J. Hyg.* 70:767, 1972.
Huang et al., "Plant-derived measles virus hemagglutinin protein induces neutralizing antibodies in mice," *Vaccine* 19(15-16): 2163-2171, 2001.
Hunter et al., "Messenger RNA for the Coat Protein of Tobacco Mosaic Virus," *Nature* 260: 759-760, 1976.
Ishida et al., "A combinatorial approach to producing sterically stabilized (Stealth) immunoliposomal drugs," *FEBS Lett.* 460(1):129-33, 1999.
Ishikawa et al., "In Vitro Mutagenesis of the Putative Replicase Genes of Tobacco Mosaic Virus," *Nucleic Acids Res.* 14: 8291-8308, 1986.
Jaspars et al., "Plant Viruses With a Multipartite Genome," *Adv. Virus Res.* 19: 37-149, 1974.
Jefferson et al., "GUS fusions: beta-glucuronidase as a sensitive and versatile gene fusion marker in higher plants," *EMBO J* 6: 3901-3907, 1987.
Johnson et al., "Respiratory syncytial virus (RSV) G glycoprotein is not necessary for vaccine-enhanced disease induced by immunization with formalin-inactivated RSV," *J. Virol* 78(11):6024-32, 2004.
Kao et al., "A Method for High-frequency Intergeneric Fusion of Plant Protoplasts," *Planta* 115:355, 1974.
Kapila et al., "An *Agrobacterium*-mediated transient gene expression system for intact leaves," *Plant Sci.* 122:101-108, 1997.
Kapusta et al., "A plant-derived edible vaccine against hepatitis B virus," *FASEB J* 13:1796-1799, 1999.
Karlin and Altschul, "Methods for assessing the statistical significance of molecular sequence features by using general scoring schemes," *Proc. Natl. Acad. Sci. USA* 87:2264-2268, 1990.
Karlin and Altschul, "Applications and statistics for multiple high-scoring segments in molecular sequences," *Proc. Natl. Acad. Sci. USA* 90:5873-5877,1993.
Kikkert et al., "Biological Projectiles (Phage, Yeast, Bacteria) for Genetic Transformation of Plants," *In Vitro Cell. Dev. Bio.—Plant* 35(1):43-50, 1999.
Klein et al., "High-velocity microprojectiles for delivering nucleic acids into living cells," *Nature* 327:70-73, 1987.
Knapp et al., "Conundrum of the Lack of Defective RNAs (dRNAs) Associated with Tobamovirus Infections: dRNAs that Can Move Are Not Replicated by the Wild-Type Virus; dRNAs that Are Replicated by the Wild-Type Virus Do Not Move," *J. Virol.* 75:5518, 1002.
Knudsen and Muller, "Transformation of the developing barley endosperm by particle bombardment," *Planta* 185:330-336, 1991.
Kohler and Milstein, "Continuous cultures of fused cells secreting antibody of predefined specificity," *Nature* 256: 495, 1975.
Krebber et al., "Reliable cloning of functional antibody variable domains from hybridomas and spleen cell repertoires employing a reengineered phage display system," *J. Immunol. Meth.* 201: 35-55, 1997.
Krens et al., "In vitro transformation of plant protoplasts with Ti-plasmid DNA," *Nature* 296:72-74, 1982.
Kubler-Kielb et al., "Long-lasting and transmission-blocking activity of antibodies to *Plasmodium falciparum* elicited in mice by protein conjugates of Pfs25," *Proc. Natl. Acad. Sci. USA* 104(1): 293-298, 2007.
Kumagai, et al., "Rapid, High-Level Expression of Glycosylated Rice α-Amylase in Transfected Plants by an RNA Viral Vector," *Gene* 245: 169-174, 2000.
Lambkin et al., "Strong local and systemic protective immunity induced in the ferret model by an intranasal virosome-formulated influenza subunit vaccine," *Vaccine* 22:4390, 2004.
Lawton et al., "Expression of a Soybean 3-Conclycinin Gene under the Control of the Cauliflower Mosaic Virus Virus 35S and 19S Promoters in Transformed Petunia Tissues," *Plant Mol. Biol.* 9: 315-324, 1987.
Leite et al., "Expression of correctly processed human growth hormone in seeds of transgenic tobacco plants," *Molecular Breeding* 6: 47-53, 2000.
Lensen, A. et al., "Measurement by membrane feeding of reduction in *Plasmodium falciparum* transmission induced by endemic sera," *Trans R Soc Trop Med Hyg.* 90(1):20-22, 1996.
Lewandowski and Dawson, "Deletion of Internal Sequences Results in Tobacco Mosaic Virus Defective RNAs That Accumulate to High Levels without Interfering with Replication of the Helper Virus," *Virology* 251:427-437, 1998.
Li et al , "Immunization with recombinant beta-tubulin from *Trypanosoma evansi* induced protection against *T. evansi, T. equiperdum* and *T. b. brucei* infection in mice," *Parasite Immunology* 29:191-199, 2007.
Lim et al., "An Anthrax Lethal Factor-Neutralizing Monoclonal Antibody Protects Rats before and after Challenge with Anthrax Toxin," *Infection and Immunity* 73:6547,2005.
Lin et al., "Treatment of Established Tumors with a Novel Vaccine That Enhances Major Histocompatibility Class II Presentation of Tumor Antigen," *Cancer Research* 56:21, 1996.
Little et al., "Passive Protection by Polyclonal Antibodies against *Bacillus anthracis* Infection in Guinea Pigs," *Infect. Immun.* 65:5171-5175, 1997.
Loesch-Fries et al., "Expression of Alfalfa Mosaic Virus RNA 4 cDNA Transcripts In Vitro and In Vivo," *Virology* 146: 177-187, 1985.
Lorence and Verpoorte, "Gene transfer and expression in plants," *Methods Mol. Biol.* 267:329-50, 2004.
Lubega et al., "Immunization with a tubulin-rich preparation from *Trypanosoma brucei* confers broad protection against African trypanosomosis," *Exp. Parasitol.* 102:9-22, 2002.
Lubega et al., "*Trypanosoma brucei*: anti-tubulin antibodies specifically inhibit trypanosome growth in culture," *Exp. Parasitol.* 102:134-142, 2002.
Maassab et al., "Evaluation of a Cold-Recombinant Influenza Virus Vaccine in Ferrets," *J. Infect. Dis.* 146(6): 780-790, 1982.
Maliga et al., "Transient Cycloheximide Resistance in a Tobacco Cell Line," *Mol. Gen. Genet.* 149: 267-271, 1976.
Mathew, Plant Viruses Online—Cassava Indian mosaic bigeminvirus (http://imagels.uidaho.eduivide/), downloaded on Feb. 21, 2006, 5 pgs.
Mattila et al., "Fidelity of DNA synthesis by the Thermococcus litoralis DNA polymerase—an exttemely heat stable enzyme with proofreading activity," *Nucleic Acids Res.* 19:4967, 1991.
McCormick et al., "Rapid Production of Specific Vaccines for Lymphoma by Expression of the Tumor-Derived Single-Chain Fv Epitopes in Tobacco Plants" *Proc. Natl. Acad. Sci. USA* 96: 703-708, 1999.
McHugh et al., "Improved stability of a protein vaccine through elimination of a partially unfolded state," *Protein Science* 13: 2736-2743, 2004.

(56) References Cited

OTHER PUBLICATIONS

Mellin et al., "Human Papillomavirus (HPV) DNA in Tonsillar Cancer: Clinical Correlates, Rise of Relapse, and Survival," *Int. J. Cancer* 89:300-304, 2000.
Menczel et al. "Streptomycin Resistant and Sensitive Somatic Hybrids of *Nicotiana tabacum* + *Nicotiana knightiana*: Correlation of Resistance to *N. tabacum* Plastids," *Theor. Appl. Genet.* 59: 191-195, 1981.
Meshi et al., "Function of the 30 kd Protein of Tobacco Mosaic Virus: Involvement in Cell-to-Cell Movement and Dispensability for Replication," *EMBO J.* 6: 2557-63, 1987.
Mett et al., "A plant-produced influenza subunit vaccine protects ferrets against virus challenge," *Influenza and Other Respiratory Viruses* 2(1): 33-40, 2008.
Mett et al., "A plant-produced plague vaccine candidate confers protection to monkeys," *Vaccine* 25(16): 3014-3017, 2007.
Moayeri et al., "The roles of anthrax toxin in pathogenesis," *Curr Opin Michrobiol* 7(1):19-24, 2004.
Modelska et al., "Immunization against rabies with plant-derived antigen," *Proc. Nati. Acad. Sci. USA* 95:2481-2485, 1998.
Moreira et al., "A Thermostable Maltose-tolerant α-anylase from *Asperillgus tamarii*," *J. Basic Microbiology* 44: 29-35, 2004.
Murashige et al., "A Revised Medium for Rapid Growth and Bio Assays with Tobacco Tissue Cultures," *Physiologia Plantarum*, 15:473, 1962.
Musiychuk et al., "A launch vector for the production of vaccine antigens in plants," *Influenza and Other Respiratory Viruses* 1:1, 2007.
Musiychuk et al., "Preparation and properties of *Clostridium thermocellum* lichenase deletion variants and their use for construction of bifunctional hybrid proteins," *Biochemistry(MOSC)* 65(12): 1397-1402, 2000.
Nagy et al., "Thermal stability of chemically denatured green fluorescent protein (GFP)—A preliminary study," *Thermochimica Acta* 410(1): 161-163, 2004.
Nass, "Anthrax Vaccine—Model of a Response to the Biologic Warfare Threat," *Infect. Dis. Clin. North Am.* 13: 187-208, 1999.
NCBI GenBank Accession No. ABP96852, "Influenza A virus" (A/Egypt/2616-NAMRU3/2007(H5N1)) hemagglutinin (HA) gene, complete CDS, 30, Apr. 2007.
NCBI GenBank Accession No. AAS93885, "Influenza A virus" (A/Cheju/274/2002(H3N2)) neuraminidase (NA) gene, complete CDS, 25, Apr. 2004.
Neeleman et al., "Role of Alfalfa Mosaic Virus Coat Protein Gene in Symptom Formation," *Virology* 181: 687-693, 1991.
Neeleman et al., "Infection of Tobacco with Alfalfa Mosaic Virus cDNAs Sheds Light on the Early Function of the Coat Protein," *Virology* 196: 883-887, 1993.
Park et al., "Molecular Biology of Cervical Cancer and Its Precursors," *Cancer* 76:1902-1913, 1995.
Parkhill et al., "Genome sequence of *Yersinia pestis*, the causative agent of plague," *Nature* 413:523-7, 2001.
Peres et al., 2001 , "Shoot regeneration capacity from roots and transgenic hairy roots of tomato cultivars and wild related species," *Plant Cell, Tissue, and Organ Culture* 65:37-44, 2001.
Petosa et al., "Crystal structure of the anthrax toxin protective antigen," *Nature* 385:833-838, 1997.
Pilon-Smits et al., "Overexpression of ATP Sulfurylase in Indian Mustard Leads to Increased Selenate Uptake, Reduction, and Tolerance," *Plant Physiol.* 119(1): 123-132, 1999.
Piruzian et al., "A reporter system for prokaryotic and eukaryotic cells based on the thermostable lichenase from *Clostridium thermocellum*," *Mol Genet Genomics* 266(5): 778-86, 2001.
Piruzian et al., "The use of a thermostable B-glucanase gene from *Clostridium thermocellum* as a reporter gene in plants," *Mol Gen Genet* 257(50): 561-7, 1998.
Potter et al., "Immunity to Influenza in Ferrets II. Influence of Adjuvants on Immunization," *Br. J. Exp. Pathol.* 53:168, 1972.
Potter et al., "Immunity to Influenza in Ferrets VI. Immunization with Adjuvanted Vaccines," *Arch. Gesamte Virusforsch.* 42:285, 1973.
Potter et al., "Immunity to influenza in ferrets V. Immunization with inactivated virus in adjuvant 65," *J. Hyq. Lond.* 71:97, 1973.
Qian et al., "Conjugating recombinant proteins to Pseudomonas aeruginosa ExoProtein A: A strategy for enhancing immunogenicity of malaria vaccine candidate," *Vaccine* 25(20): 3923-3933, 2007.
Qing et al., "Transformation of Pakchoi (*Brassica rapa* L. ssp. *chinensis*) by *Agrobacterium* Infiltration," *Molecular Breeding* 1:67-72, 2000.
Rao and Ravishankar, "Plant cell cultures: Chemical factories of secondary metabolites," *Biotechnol. Adv.* 20:101-153, 2002.
Rasooly-Balaban, "Trypanosome microtubule-associated protein p15 as a vaccine for the prevention of African sleeping sickness," *Vaccine* 22(8): 1007-1015, 2004.
Reinstein et al., "Degradation of the E7 human papillomavirus oncoprotein by the ubiquitin-proteasome system: targeting via ubiquitination of the N-terminal residue," *Oncogene* 19: 5944-5950, 2000.
Riva et al., "*Agrobacterium tumefaciens*: a natural tool for plant transformation, "*EJB Electronic J. Biotech.* 1(3): 118-133, 1998.
Saito et al., "Long-Distance Movement and Viral Assembly of Tobacco Mosaic Virus Mutants" *Virology* 176: 329-336, 1990.
Santi et al., "Protection conferred by recombinant *Yersinia pestis* antigens produced by a rapid and highly scalable plant expression system," *Proc. Natl. Acad. Sci. USA* 103(4): 861-866, 2006.
Scheiblauer et al., "Pathogenicity of influenza A/Seal/Mass/1/80 virus mutants for mammalian species," *Arch Virol*, 140: 341-384, 1995.
Schell et al., "Transgenic Plants as Tools to Study the Molecular Organization of Plant Genes," *Science* 237: 1176-1183, 1987.
Seedorf et al., "Human Papillomavirus Type 16 DNA Sequence," *Virology* 145:181, 1985.
Sen et al., "Developments in Directed Evolution for Improving Enzyme Functions," *Appl Biochem Biotechnol.* 143(3):212-23, 2007.
Shima et al., "Hyperthermaphilic and salt-dependent formytransferase from Methanopyrus kanleri," *Biochem Soc. Trans.* 32:269-72, 2004.
Shivprasad et al., "Heterologous Sequences Greatly Affect Foreign Gene Expression in Tobacco Mosaic Virus-Based Vectors," *Virology* 255(2):312-23, 1999.
Singh et al., "Gln277 and Phe544 residues are involved in thermal inactivation of protective antigen of *Bacillus anthracis," Biochem. Biophys. Res. Commun.* 296: 1058-1062, 2002.
Singh et al., "Study of Immunization against Anthrax with the Purified Recombinant Protective Antigen of *Bacillus anthracis," Infect. Immun.* 66: 3447-3448, 1998.
Singh et al., "Thermal inactivation of protective antigen of *Bacillus anthracis* and its prevention by polyol osmolytes," *Biochem. Biophys. Res. Commun.* 322: 1029-1037, 2004.
Smahel et al., "Modified HPV16 E7 Genes as DNA Vaccine against E7-Containing Oncogenic Cells," *Virology* 281: 231-238, 2001.
Snow et al., "The global distribution of clinical episodes of *Plasmodium falciparum* malaria," Nature 434:214-7, 2005.
Soini et al., "Presence of human papillomavirus DNA and abnormal p53 protein accumulation in lung carcinoma," *Thorax* 51:887-893, 1996.
Spilliaert et al., "Cloning and sequencing of a Rhodothermus marinus gene, bg1A, coding for a thermostable beta-glucanase and its expression in *Escherichia coli," Eur. J. Biochem.* 224(3):923-930, 1994.
Stewart et al., "Mutant barley (1→3,1→4)-β-glucan endohydrolases with enhanced thermostability," *Protein Engineering* 14(4): 245-253, 2001.
Tacket et al., "Human Immune Responses to a Novel Norwalk Virus Vaccine Delivered in Transgenic Potatoes," *J. Infect. Dis.* 182:302-305, 2000.
Thanavala et al., "Immunogenicity in humans of an edible vaccine for hepatitis B," *Proc. Natl. Acad. Sci. USA* 102:3378-3382, 2005.
The World Health Organization Global Influenza Program Surveillance Network, "Evolution of H5N1 Avian Influenza Viruses in Asia," *Emerging Infectious Diseases* 11(10): 1515-1521, 2005.
Thomas et al., "HPV-18 E6 mediated inhibition of p53 DNA binding activity is independent of E6 induced degradation," *Oncogene* 10:261-8, 1995.

(56) References Cited

OTHER PUBLICATIONS

Toms et al., "Behaviour in Ferrets of Swine Influenza Virus Isolated from Man," *The Lancet* 309(8002): 68-71, 1977.
Torchilin et al., "p-Nitrophenylcarbonyl-PEG-PE-liposomes: fast and simple attachment of speciéc ligands, including monoclonal antibodies, to distal ends of PEG chains via p-nitrophenylcarbonyl groups," *Biochim Biophys Acta* 1511(2):397-411, 2001.
Tsai et al., "Crystal structure of a natural circularly permuted jellyroll protein: 1,3-1,4-beta-D-glucanase from Fibrobacter succinogens," *J. Mol. Biol.* 330(3):607-20, 2003.
Turpen et al., "Transfection of whole plants from wounds inoculated with *Agrobacterium tumefaciens* containing cDNA of tobacco mosaic virus," *J. Virol, Methods* 42:227, 1993.
UniProt Database accession No. P04107 Nov. 1, 1986.
Van der Kolk et al., "Evaluation of the standard membrane feeding assay (SMFA) for the determination of malaria transmission-reducing activity using empirical data," *Parasitology* 130(Pt 1): 13-22, 2005 (with Erratum in: *Parasitology* 131(Pt 4):578, 2005).
Van Der Kuyl et al., "Complementation and Recombination between Alfalfa Mosaic Virus RNA3 Mutants in Tobacco Plants," *Virology* 183:731-738, 1991.
Van Der Kuyl et al., "Role of Alfalfa Mosaic Virus Coat Protein in Regulation of the Balance between Viral Plus and Minus Strand RNA Synthesis" *Virology* 185:496-499, 1991.
Van Der Vossen, et al., "Early and Late Functions of Alfalfa Mosaic Virus Coat Protein Can Be Mutated Separately" *Virology* 202: 891-903, 1994.
Verch et al., "Expression and assembly of a full-length monoclonal antibody in plants using a plant virus vector," *J. Immunol. Methods* 220: 69-75, 1998.
Voinnet et al., "An enhanced transient expression system in plants based on suppression of gene silencing by the p19 protein of tomato bushy stunt virus," *Plant J.* 33:949-56, 2003.
Volten-Doting, Plant Viruses Online (http://image.fs.uidaho.edu/vide/descr009.htm) (downloaded May 18, 2002) (11 pgs.)
Wagner et al., "Plant virus expression systems for transient production of recombinant allergens in *Nicotiana benthamiana*," *Methods: A Companion to Methods in Enzymology* 32(3): 228-232, 2004.
Wang et al, "Immunogenicity of *Plasmodium* yoelii merozoite surface protein 4/5 produced in transgenic plants," *Int. J. Parasitol.* 38(1): 103-110, 2007.
Wang et al., "Structural Basis for Thermostability of β-Glycosidase from the Thermophilic Eubacterium Thermus Nonproteolyticus HG102," *J. Bacteriol.* 185: 4248-55, 2003.
Webster et al., "Measles virus hemagglutinin protein expressed in transgenic lettuce induces neutralizing antibodies in mice following mucosal vaccination," *Vaccine* 24(17): 3538-3544, 2006.
Webster et al., "Protection of ferrets against influenza challenge with a DNA vaccine to the haemagglutinin," *Vaccine* 12(16): 1495-1498, 1994.
Wiesmuller et al., "Peptide Vaccines and Peptide Libraries," *Biol. Chem.* 382(4): 571-9, 2001.
Williamson et al., "Human Immune Response to a Plague Vaccine Comprising Recombinant F1 and V Antigens," *Infect. Immun.* 73(6):3598-608, 2005.
Williamson et al., "A single dose sub-unit vaccine protects against pneumonic plague," *Vaccine* 19:566-71, 2000.
Williamson et al., "A new improved sub-unit vaccine for plague: the basis of protection," *FEMS ImmunoL Med. Microbiol.* 12:223-30, 1995.
Wilson et al., "Structure of the haemagglutinin membrane glycoprotein of influenza virus at 3 Å resolution," *Nature* 289:366, 1981.
Woo, "The Haematocrit Centrifuge Technique for the Diagnosis of African Trypanosomiasis," *Acta Tropica*, 27:384, 1970.
Yusibov et al., "Antigens Produced in Plants by Infection with Chimeric Plant Viruses Immunize Against Rabies Virus and HIV-1," *Proc. Natl. Acad. Sci. USA* 94: 5784-5788, 1997.
Yusibov et al., "N-Terminal Basic Amino Acids of Alfalfa Mosaic Virus Coat Protein Involved in the Initiation of Infection," *Virology* 208: 405-407, 1995.
Yusibov, et al., "Functional Significance of Three Basic N-Terminal Amino Acids of Alfalfa Mosaic Virus Coat Protein," *Virology* 242: 1-5, 1998.
Yusibov et al., "Purification, characterization, assembly and crystallization of assembled alfalfa mosaic virus coat protein expressed in *Escherichia coli*," *J. Gen. Virol.* 77:567-573, 1996.
Yusibov et al., "Expression in plants and immunogenicity of plant virus-based experimental rabies vaccine" *Vaccine* 20:3155-3164, 2002.
Zumbach et al., "Antibodies Against Oncoproteins E6 and E7 of Human Papillomavirus Types 16 and 18 in Patients with Head-and-Neck Squamous-Cell Carcinoma," *Int. J. Cancer* 85:815-818, 2000.
Advisory Action dated Jan. 15, 2010 for U.S. Appl. No. 11/706,568 (3 pgs.).
Communication dated Sep. 23, 2009 for European Appln. No. 04 776 107.7 (3 pgs.).
Communication dated Apr. 21, 2010 for European Appln. No. 04 776 107.7 (4 pgs.).
Communication dated May 20, 2010 for European Appln. No. 04 776 107.7 (3 pgs.).
International Preliminary Report on Patentability dated Aug. 19, 2008 for Int'l. Appln. No. PCT/US07/003948 (6 pgs.).
International Preliminary Report on Patentability dated Aug. 19, 2008 for Int'l. Appln. No. PCT/US07/003973 (6 pgs.).
International Preliminary Report on Patentability dated Aug. 19, 2008 for Int'l. Appln. No. PCT/US07/003969 (6 pgs.).
International Preliminary Report on Patentability dated Nov. 3, 2009 for Int'l. Appln. No. PCT/US08/061782 (7 pgs).
International Preliminary Report on Patentability dated Jan. 12, 2010 for International Appln. No. PCT/US08/069860 (5 pgs.).
International Preliminary Report on Patentability dated Mar. 4, 2010 for Int'l. Appln. No. PCT/US08/073776 (6 pgs.).
International Preliminary Report on Patentability dated Mar. 29, 2011 for Int'l. Appln. No. PCT/US09/058669 (12 pgs.).
International Search Report and Written Opinion dated Aug. 3, 2007 for Int'l. Appln. No. PCT/US07/003973 (9 pgs.).
International Search Report and Written Opinion dated Jun. 18, 2008 for Int'l. Appln. No. PCT/US07/003948 (9 pgs.).
International Search Report and Written Opinion dated Sep. 4, 2007 for Int'l. Appln. No. PCT/US07/003969 (10 pgs.).
International Search Report and Written Opinion dated Oct. 21, 2008 for Intl. Appln. No. PCT/US08/061782 (10 pgs.).
International Search Report and Written Opinion dated Apr. 24, 2009 for Int'l. Appln. No. PCT/US08/073776 (11 pgs.).
International Search Report dated Dec. 23, 2005 for International Appln. No. PCT/US04/16452 (2 pgs.).
International Search Report and Written Opinion dated May 29, 2009 for International Appln. No. PCT/US2008/069860 (8 pgs.).
International Search Report and Written Opinion dated May 19, 2010 for International Appln. No. PCT/US2009/058669 (21 pgs.).
Office Action (non-final) dated Nov. 4, 2008 for U.S. Appl. No. 11/706,568 (7 pgs.).
Office Action (non-final) dated Jan. 6, 2009 for U.S. Appl. No. 11/706,568 (8 pgs.).
Office Action (final) dated Jul. 15, 2009 for U.S. Appl. No. 11/706,568 (7 pgs.).
Supplementary European Search Report dated Dec. 5, 2006 for European Appln. No. 04 776 107.7 (2 pgs.).
Supplementary European Search Report dated May 5, 2010 for European Appln. No. EP 07750784 (8 pgs.).
Supplementary European Search Report dated Jun. 9, 2010 for European Appln. No. EP 08 78 0572 (5 pgs.).
U.S. Appl. No. 60/652,186, filed Feb. 11, 2005, entitled "Production of Foreign Nucleic Acids and Polypeptides in Sprout Systems" by Ensley, et al.
U.S. Appl. No. 11/061,980, filed Feb. 18, 2005, entitled "Systems and Methods for Clonal Expression in Plants".
Air, "Mechanism of antigenic variation in an individual epitope on influenza virus N9 neuraminidase," *J. Virol.*, 64(12):5797-5803, 1990.

(56) References Cited

OTHER PUBLICATIONS

Aymard et al., "Role of antineuraminidase antibodies in protection against influenza," *Bulletin de l'Academie Nationale de Medicine*, 182(8):1723-1736, 1998 (with English abstract).

Aymard et al., "Neuraminidase assays," *Dev. Biol. (Basel)*, 115:75-83, 2003.

Barbas et al., "Assembly of combinatorial antibody libraries on phage surfaces: the gene III site," *Proc. Natl. Acad. Sci. USA*, 88:7978-7982, 1991.

Barbas et al., "Semisynthetic combinatorial antibody libraries: a chemical solution to the diversity problem," *Proc. Natl. Acad. Sci. USA*, 89:4457-4461, 1992.

Berger et al., "Therapeutic applications of monoclonal antibodies" *Am. J. Med. Sci.*, 324(1):14-30, 2002.

Burke et al., "Cloning of large segments of exogenous DNA into yeast by means of artificial chromosome vectors," *Science*, 236:806-812, 1987.

Dawson et al., "cDNA cloning of the complete genome of tobacco mosaic virus and production of infectious transcripts," *Proc. Natl Acad. Sci. USA*, 83:1832-1836, 1986.

Floss et al., "Production of vaccines and therapeutic antibodies for veterinary applications in transgenic plants: an overview," *Transgenic Research*, 16(3):315-332, 2007.

Huber et al., "Distinct contributions of vaccine-induced immunoglobulin G1 (IgG1) and IgG2a antibodies to protective immunity against influenza," *Clin. Vaccine Immunol.*, 13:981-990, 2006.

Huse et al., "Generation of a large combinatorial library of the immunoglobulin repertoire in phage lambda," *Science*, 246:1275-1281, 1989.

Jirholt et al., "Exploiting sequence space: shuffling in vivo formed complementarity determining regions into a master framework," *Gene*, 215:471-476, 1998.

Jones et al., "Replacing the complementarity-determining regions in a human antibody with those from a mouse," *Nature*, 321:522-525, 1986.

Kang et al., "Linkage of recognition and replication functions by assembling combinatorial antibody Fab libraries along phage surfaces," *Proc. Natl. Acad. Sci. USA*, 88:4363-4366, 1991.

Katayama and Mine, "*Quillaja* saponin can modulate ovalbumin-induced IgE allergic responses through regulation of Th1/Th2 balance in a murine model," *J. Agric. Food Chem.*, 54:3271-3276, 2006.

Konieczny et al., "The combination of IgM subunits and proteolytic IgG fragments by controlled formation of interchain disulphides," *Haematologia (Budap.)*, 14:95-99, 1981.

Lee and Air, "Contacts between influenza virus N9 neuraminidase and monoclonal antibody NC10," *Virology*, 300(2):255-268, 2002.

Marillonnet et al., "Systemic *Agrobacterium tumefaciens*-mediated transfection of viral replicons for efficient transient expression in plants," *Nature Biotechnol.*, 23(6):718-723, 2005.

Mbawuike et al., "Humoral and cell-mediated immune responses of humans to inactivated influenza vaccine with or without QS21 adjuvant," *Vaccine*, 25:3263-3269, 2007.

Mett et al., "Plants as biofactories," *Biologicals*, 36(6):354-358, 2008.

Mikayama et al., "Molecular cloning and functional expression of a cDNA encoding glycosylation-inhibiting factor," *Proc. Natl. Acad. Sci. USA*, 90:10056-10060, 1993.

Morrison et al., "Chimeric human antibody molecules: Mouse antigen-binding domains with human constant region domains," *Proc. Natl. Acad. Sci. USA*, 81:6851-6855, 1984.

Morrison et al., "Production of novel immunoglobulin molecules by gene transfection," *Mt. Sinai J. Med.*, 53:175-180, 1986.

Pfitzner et al., "Isolation and characterization of cDNA clones encoding pathogenesis-related proteins from tobacco mosaic virus infected tobacco plants," *Nucl. Acids Res.*, 15(11):4449-4465, 1987.

Pruett et al., "Critical interactions in binding antibody NC41 to influenza N9 neuraminidase: amino acid contacts on the antibody heavy chain," *Biochemistry*, 37:10660-10670, 1998.

Riechmann et al., "Reshaping human antibodies for therapy," *Nature*, 332:323-327, 1988.

Rowe et al., "Detection of antibody to avian influenza A (H5N1) virus in human serum by using a combination of serologic assays," *J. Clin. Microbiol.*, 37:937-943, 1999.

Rudinger et al., "Characteristics of the amino acids as components of a peptide hormone sequence," *Peptide Hormones*, Parsons (ed.), University Park Press, Baltimore, 1976, pp. 1-7.

Sabbatini et al., "Pilot Study of a heptavalent vaccine-keyhole limpet hemocyanin conjugate plus QS21 in patients with epithelial ovarian, fallopian tube, or peritoneal cancer," *Clin. Cancer Res.*, 13:4170-4177, 2007.

Saravolac et al. "Immunoprophylactic strategies against respiratory influenza virus infection." *Vaccine*, 19(17-19):2227-2232, 2001.

Schild et al., "A single-radial-immunodiffusion technique for the assay of influenza haemagglutinin antigen," *Bull. World Health Org.*, 52:223-231, 1975.

Shimasaki et al., "Rapid diagnostics: the detection of neuraminidase activity as a technology for high-specificity targets," *Phil. Trans. R. Soc. Lond. B*, 356(1416):1925-1931, 2001.

Shoji et al, "Immunogenicity of hemagglutinin from A/Bar-headed/Goose/Qinghai/1A/05 and A/Anhui/1/05 strains of H5N1 influenza viruses produced in *Nicotiana benthamiana* plants," *Vaccine*, 27:3467-3470, 2009.

Shoji et al., "Plant-expressed HA as a seasonal influenza vaccine candidate," *Vaccine*, 26(23):2930-2934, 2008.
Soderlind et al., "Complementarity-determining region (CDR) implantation: a theme of recombination," *Immunotechnol.*, 4:279-285, 1999.
Soderlind et al., "Recombining germline-derived CDR sequences for creating diverse single framework antibody libraries," *Nature Biotechnol.*, 18:852-856, 2000.
Sweet et al., "Pathogenicity of influenza virus," *Microbiolog. Rev.*, 44(2):303-330, 1980.
Throsby et al., "Heterosubtypic neutralizing monoclonal antibodies cross-protective against H5NI and H1N1 recovered from human IgM+ memory B cells," *Plos One*, 3(12):e3942, 2008.
UniProt Database EBI Accession No. Q0PDN1, [Online] "SubName: Full=Hemagglutinin," Sep. 5, 2006.
UniProt Database EBI Accession No. A9X0E7, [Online] "SubName: Full=Hemagglutinin; Flags: Precursor," Feb. 5, 2008.
Webster et al., "Antigenic structure and variation in an influenza virus N9 neuraminidase," *J. Virol.*, 61:2910-2916, 1987.
Winter and Milstein, "Man-made antibodies," *Nature*, 349:293-299, 1991.
Yang et al., "Production and diagnostic application of monoclonal antibodies against influenza virus H5," *J. Virolog. Meth.*, 162(1-2):194-202, 2009.
Yusibov et al., "An influenza N1 neuraminidase-specific monoclonal antibody with broad inactivating activity against H5N1 viruses," *Human Antibodies*, 16:33, 2007.
Yusibov et al., "An influenza N1 neuraminidase-specific monoclonal antibody protects animal against live challenge with homologous H5N1 virus," *Human Antibodies*, 17:15, 2008.
Yusibov et al., "The potential of plant virus vectors for vaccine production," *Drugs R D*, 7(4):203-217, 2006.
Zapata et al., "Engineering linear F(ab')2 fragments for efficient production in *Escherichia coli* and enhanced antiproliferative activity," *Prot. Eng.*, 8:1057-1062, 1995.
International Preliminary Report on Patentability dated Mar. 17, 2009 for Int'l. Appln. No. PCT/US07/004103 (5 pgs.).
International Preliminary Report on Patentability dated Mar. 29, 2011 for Int'l. Appln. No. PCT/US09/058488 (13 pgs.).
International Preliminary Report on Patentability for International Appln. No. PCT/US2009/058640 dated Mar. 29, 2011 (7 pgs.).
International Search Report and Written Opinion dated Aug. 7, 2007 for Int'l. Appln. No. PCT/US07/004103 (9 pgs).
International Search Report and Written Opinion dated May 11, 2010 for International Appln. No. PCT/US2009/058488 (20 pgs.).
International Search Report and Written Opinion for International Appln. No. PCT/US2009/058640 dated Feb. 2, 2010 (13 pgs.).
International Search Report and Written Opinion dated Jan. 27, 2011 for Int'l. Appln. No. PCT/US10/050693 (7 pgs.).

(56) References Cited

OTHER PUBLICATIONS

Office Action (restriction requirement) dated Nov. 28, 2007 for U.S. Appl. No. 11/706,573 (8 pgs.).
Office Action (non-final) dated Apr. 16, 2008 for U.S. Appln. No. 11/706,573 (11 pgs.).
Office Action (non-final) dated Jan. 21, 2009 for U.S. Appl. No. 11/706,573 (10 pgs.).
Office Action (non-final) dated Feb. 22, 2010 for U.S. Appl. No. 11/706,573 (11 pgs.).
Office Action (non-final) dated Nov. 24, 2010 for U.S. Appl. No. 11/706,573 (11 pgs.).
Supplementary European Search Report dated Oct. 8, 2009 for European Appln. No. EP 07750950 (5 pgs.).

Mett et al., "A non-glycosylated, plant-produced human monoclonal antibody against anthrax protective antigen protects mice and non-human primates from *B. anthracis* spore challenge," *Human Vaccines,* 7:183-190, 2011.

Nuttall et al., "A functional antibody lacking *N*-linked glycans in efficiently folded, assembled and secreted by tobacco mesophyll protoplasts," *Plant Biotechnology Journal,* 3:497-504, 2005.

Yusibov et al., "The potential of plant virus vectors for vaccine production," *Drugs in R&D*, 7(4):203-217, 2006.

Communication—Summons to Attend Oral Proceedings dated Jan. 4, 2013 for European Appln. No. 06850507.2 (7 pgs.).

Supplemental European Search Report dated Jun. 12, 2012 for European Appln. No. 07750787.9 (12 pgs.).

Supplemental European Search Report dated Jan. 25, 2013 for European Appln. No. 08826237.3 (10 pgs.).

* cited by examiner

Half-life Study of anti-PA and anti-LF Human Monoclonal Antibodies in Rats

SEQUENCE LISTING

<160> NUMBER OF SEQ ID NOS: 70

<210> SEQ ID NO 1
<211> LENGTH: 37
<212> TYPE: DNA
<213> ORGANISM: Artificial
<220> FEATURE:
<223> OTHER INFORMATION: Constant Gamma

<400> SEQUENCE: 1
ctcgcggcct ccgaggcctc atttaccckg agacagg      37

<210> SEQ ID NO 2
<211> LENGTH: 19
<212> TYPE: DNA

```
<213> ORGANISM: Artificial
<220> FEATURE:
<223> OTHER INFORMATION: Constant Gamma

<400> SEQUENCE: 2
tcatttaccc kgagacagg                                                    19

<210> SEQ ID NO 3
<211> LENGTH: 36
<212> TYPE: DNA
<213> ORGANISM: Artificial
<220> FEATURE:
<223> OTHER INFORMATION: Constant Lambda

<400> SEQUENCE: 3
ctcgcggcct ccgaggccct aagagcattc tgragg                                 36

<210> SEQ ID NO 4
<211> LENGTH: 17
<212> TYPE: DNA
<213> ORGANISM: Artificial
<220> FEATURE:
<223> OTHER INFORMATION: Constant Lambda

<400> SEQUENCE: 4
taagagcatt ctgragg                                                      17

<210> SEQ ID NO 5
<211> LENGTH: 38
<212> TYPE: DNA
<213> ORGANISM: Artificial
<220> FEATURE:
<223> OTHER INFORMATION: Constant Kappa

<400> SEQUENCE: 5
ctcgcggcct ccgaggccct aacactctcc cctgttga                               38

<210> SEQ ID NO 6
<211> LENGTH: 19
<212> TYPE: DNA
<213> ORGANISM: Artificial
<220> FEATURE:
<223> OTHER INFORMATION: Constant Kappa

<400> SEQUENCE: 6
taacactctc ccctgttga                                                    19

<210> SEQ ID NO 7
<211> LENGTH: 35
<212> TYPE: DNA
<213> ORGANISM: Artificial
<220> FEATURE:
<223> OTHER INFORMATION: Variable Heavy

<400> SEQUENCE: 7
ctcgcggccc agccggccat ggactgsayc tggag                                  35

<210> SEQ ID NO 8
<211> LENGTH: 38
<212> TYPE: DNA
<213> ORGANISM: Artificial
<220> FEATURE:
<223> OTHER INFORMATION: Variable Heavy

<400> SEQUENCE: 8
ctcgcggccc agccggccat ggacayactt tgctmcac                               38
```

```
<210> SEQ ID NO 9
<211> LENGTH: 38
<212> TYPE: DNA
<213> ORGANISM: Artificial
<220> FEATURE:
<223> OTHER INFORMATION: Variable Heavy

<400> SEQUENCE: 9
ctcgcggccc agccggccat gsagttkkgg ctghgctg                              38

<210> SEQ ID NO 10
<211> LENGTH: 38
<212> TYPE: DNA
<213> ORGANISM: Artificial
<220> FEATURE:
<223> OTHER INFORMATION: Variable Heavy

<400> SEQUENCE: 10
ctcgcggccc agccggccat gaaacacctg tggttctt                              38

<210> SEQ ID NO 11
<211> LENGTH: 38
<212> TYPE: DNA
<213> ORGANISM: Artificial
<220> FEATURE:
<223> OTHER INFORMATION: Variable Heavy

<400> SEQUENCE: 11
ctcgcggccc agccggccat ggggtcaacc gccatcct                              38

<210> SEQ ID NO 12
<211> LENGTH: 38
<212> TYPE: DNA
<213> ORGANISM: Artificial
<220> FEATURE:
<223> OTHER INFORMATION: Variable Heavy

<400> SEQUENCE: 12
ctcgcggccc agccggccat gtctgtctcc ttcctcat                              38

<210> SEQ ID NO 13
<211> LENGTH: 17
<212> TYPE: DNA
<213> ORGANISM: Artificial
<220> FEATURE:
<223> OTHER INFORMATION: Variable Heavy

<400> SEQUENCE: 13
atggactgsa yctggag                                                    17

<210> SEQ ID NO 14
<211> LENGTH: 20
<212> TYPE: DNA
<213> ORGANISM: Artificial
<220> FEATURE:
<223> OTHER INFORMATION: Variable Heavy

<400> SEQUENCE: 14
atggacayac tttgctmcac                                                 20

<210> SEQ ID NO 15
<211> LENGTH: 20
<212> TYPE: DNA
<213> ORGANISM: Artificial
<220> FEATURE:
```

```
<223> OTHER INFORMATION: Variable Heavy

<400> SEQUENCE: 15
atgsagttkk ggctghgctg                                                   20

<210> SEQ ID NO 16
<211> LENGTH: 20
<212> TYPE: DNA
<213> ORGANISM: Artificial
<220> FEATURE:
<223> OTHER INFORMATION: Variable Heavy

<400> SEQUENCE: 16
atgaaacacc tgtggttctt                                                   20

<210> SEQ ID NO 17
<211> LENGTH: 20
<212> TYPE: DNA
<213> ORGANISM: Artificial
<220> FEATURE:
<223> OTHER INFORMATION: Variable Heavy

<400> SEQUENCE: 17
atggggtcaa ccgccatcct                                                   20

<210> SEQ ID NO 18
<211> LENGTH: 20
<212> TYPE: DNA
<213> ORGANISM: Artificial
<220> FEATURE:
<223> OTHER INFORMATION: Variable Heavy

<400> SEQUENCE: 18
atgtctgtct ccttcctcat                                                   20

<210> SEQ ID NO 19
<211> LENGTH: 36
<212> TYPE: DNA
<213> ORGANISM: Artificial
<220> FEATURE:
<223> OTHER INFORMATION: Variable Lambda

<400> SEQUENCE: 19
ctcgcggccc agccggccat grccdgstyt cctctc                                 36

<210> SEQ ID NO 20
<211> LENGTH: 38
<212> TYPE: DNA
<213> ORGANISM: Artificial
<220> FEATURE:
<223> OTHER INFORMATION: Variable Lambda

<400> SEQUENCE: 20
ctcgcggccc agccggccat ggcctgggct ctgctgct                               38

<210> SEQ ID NO 21
<211> LENGTH: 36
<212> TYPE: DNA
<213> ORGANISM: Artificial
<220> FEATURE:
<223> OTHER INFORMATION: Variable Lambda

<400> SEQUENCE: 21
ctcgcggccc agccggccat ggcctggryc vytctc                                 36
```

```
<210> SEQ ID NO 22
<211> LENGTH: 38
<212> TYPE: DNA
<213> ORGANISM: Artificial
<220> FEATURE:
<223> OTHER INFORMATION: Variable Lambda

<400> SEQUENCE: 22
ctcgcggccc agccggccat ggcctgggtc tccttcta                              38

<210> SEQ ID NO 23
<211> LENGTH: 38
<212> TYPE: DNA
<213> ORGANISM: Artificial
<220> FEATURE:
<223> OTHER INFORMATION: Variable Lambda

<400> SEQUENCE: 23
ctcgcggccc agccggccat ggcctggact cytctcct                              38

<210> SEQ ID NO 24
<211> LENGTH: 38
<212> TYPE: DNA
<213> ORGANISM: Artificial
<220> FEATURE:
<223> OTHER INFORMATION: Variable Lambda

<400> SEQUENCE: 24
ctcgcggccc agccggccat ggcctgggct ccactact                              38

<210> SEQ ID NO 25
<211> LENGTH: 38
<212> TYPE: DNA
<213> ORGANISM: Artificial
<220> FEATURE:
<223> OTHER INFORMATION: Variable Lambda

<400> SEQUENCE: 25
ctcgcggccc agccggccat ggcctggact cctctctt                              38

<210> SEQ ID NO 26
<211> LENGTH: 38
<212> TYPE: DNA
<213> ORGANISM: Artificial
<220> FEATURE:
<223> OTHER INFORMATION: Variable Lambda

<400> SEQUENCE: 26
ctcgcggccc agccggccat gscctggrts atgcttct                              38

<210> SEQ ID NO 27
<211> LENGTH: 18
<212> TYPE: DNA
<213> ORGANISM: Artificial
<220> FEATURE:
<223> OTHER INFORMATION: Variable Lambda

<400> SEQUENCE: 27
atgrccdgst ytcctctc                                                    18

<210> SEQ ID NO 28
<211> LENGTH: 20
<212> TYPE: DNA
<213> ORGANISM: Artificial
<220> FEATURE:
<223> OTHER INFORMATION: Variable Lambda
```

<400> SEQUENCE: 28
atggcctggg ctctgctgct                                        20

<210> SEQ ID NO 29
<211> LENGTH: 18
<212> TYPE: DNA
<213> ORGANISM: Artificial
<220> FEATURE:
<223> OTHER INFORMATION: Variable Lambda

<400> SEQUENCE: 29
atggcctggr ycvytctc                                          18

<210> SEQ ID NO 30
<211> LENGTH: 20
<212> TYPE: DNA
<213> ORGANISM: Artificial
<220> FEATURE:
<223> OTHER INFORMATION: Variable Lambda

<400> SEQUENCE: 30
atggcctggg tctccttcta                                        20

<210> SEQ ID NO 31
<211> LENGTH: 20
<212> TYPE: DNA
<213> ORGANISM: Artificial
<220> FEATURE:
<223> OTHER INFORMATION: Variable Lambda

<400> SEQUENCE: 31
atggcctgga ctcytctcct                                        20

<210> SEQ ID NO 32
<211> LENGTH: 20
<212> TYPE: DNA
<213> ORGANISM: Artificial
<220> FEATURE:
<223> OTHER INFORMATION: Variable Lambda

<400> SEQUENCE: 32
atggcctggg ctccactact                                        20

<210> SEQ ID NO 33
<211> LENGTH: 20
<212> TYPE: DNA
<213> ORGANISM: Artificial
<220> FEATURE:
<223> OTHER INFORMATION: Variable Lambda

<400> SEQUENCE: 33
atggcctgga ctcctctctt                                        20

<210> SEQ ID NO 34
<211> LENGTH: 20
<212> TYPE: DNA
<213> ORGANISM: Artificial
<220> FEATURE:
<223> OTHER INFORMATION: Variable Lambda

<400> SEQUENCE: 34
atgscctggr tsatgcttct                                        20

<210> SEQ ID NO 35
<211> LENGTH: 38

```
<212> TYPE: DNA
<213> ORGANISM: Artificial
<220> FEATURE:
<223> OTHER INFORMATION: Variable Kappa

<400> SEQUENCE: 35
ctcgcggccc agccggccat ggacatgagg gtccycgc                                    38

<210> SEQ ID NO 36
<211> LENGTH: 38
<212> TYPE: DNA
<213> ORGANISM: Artificial
<220> FEATURE:
<223> OTHER INFORMATION: Variable Kappa

<400> SEQUENCE: 36
ctcgcggccc agccggccat gaggstccyt gctcagct                                    38

<210> SEQ ID NO 37
<211> LENGTH: 38
<212> TYPE: DNA
<213> ORGANISM: Artificial
<220> FEATURE:
<223> OTHER INFORMATION: Variable Kappa

<400> SEQUENCE: 37
ctcgcggccc agccggccat ggaarcccca gcgcagct                                    38

<210> SEQ ID NO 38
<211> LENGTH: 38
<212> TYPE: DNA
<213> ORGANISM: Artificial
<220> FEATURE:
<223> OTHER INFORMATION: Variable Kappa

<400> SEQUENCE: 38
ctcgcggccc agccggccat ggtgttgcag acccaggt                                    38

<210> SEQ ID NO 39
<211> LENGTH: 38
<212> TYPE: DNA
<213> ORGANISM: Artificial
<220> FEATURE:
<223> OTHER INFORMATION: Variable Kappa

<400> SEQUENCE: 39
ctcgcggccc agccggccat ggggtcccag gttcacct                                    38

<210> SEQ ID NO 40
<211> LENGTH: 20
<212> TYPE: DNA
<213> ORGANISM: Artificial
<220> FEATURE:
<223> OTHER INFORMATION: Variable Kappa

<400> SEQUENCE: 40
atggacatga gggtccycgc                                                        20

<210> SEQ ID NO 41
<211> LENGTH: 20
<212> TYPE: DNA
<213> ORGANISM: Artificial
<220> FEATURE:
<223> OTHER INFORMATION: Variable Kappa

<400> SEQUENCE: 41
```

```
atgaggstcc ytgctcagct                                              20

<210> SEQ ID NO 42
<211> LENGTH: 20
<212> TYPE: DNA
<213> ORGANISM: Artificial
<220> FEATURE:
<223> OTHER INFORMATION: Variable Kappa

<400> SEQUENCE: 42
atggaarccc cagcgcagct                                              20

<210> SEQ ID NO 43
<211> LENGTH: 20
<212> TYPE: DNA
<213> ORGANISM: Artificial
<220> FEATURE:
<223> OTHER INFORMATION: Variable Kappa

<400> SEQUENCE: 43
atggtgttgc agacccaggt                                              20

<210> SEQ ID NO 44
<211> LENGTH: 20
<212> TYPE: DNA
<213> ORGANISM: Artificial
<220> FEATURE:
<223> OTHER INFORMATION: Variable Kappa

<400> SEQUENCE: 44
atggggtccc aggttcacct                                              20

<210> SEQ ID NO 45
<211> LENGTH: 708
<212> TYPE: DNA
<213> ORGANISM: Artificial
<220> FEATURE:
<223> OTHER INFORMATION: DNA sequence of PA-1 huMab Kappa light chain
      cDNA

<400> SEQUENCE: 45
atggaagccc cagcgcagct tctcttcctc ctgctactct ggctcccaga taccaccgga    60
gaaattgtgt tgacgcagtc tccaggcacc ctgtctttgt ctccagggga aagagccacc   120
ctctcctgca gggccagtca gagtgttagc tacagctcct tagcctggta ccagcagaaa   180
cctggccagg ctcccagcct cctcatctat ggtgcatcca gcagggccac tggcatccca   240
gacaggttca gtggcagtgg gtctgggcca gacttcactc tcaccatcag cagactggag   300
cctgaagatt ttgcagttta ttactgtcag cactatggta actcaccgta cacttttggc   360
caggggacca agctggagat caaacgaact gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca aagcagacta cgagaaacac aaagtctacg cctgcgaagt cacccatcag   660
ggcctgagct cgcccgtcac aaagagcttc aacaggggag agtgttag               708

<210> SEQ ID NO 46
<211> LENGTH: 235
<212> TYPE: PRT
<213> ORGANISM: Artificial
<220> FEATURE:
```

<223> OTHER INFORMATION: Amino acid sequence of PA-1 huMab Kappa light
      chain

<400> SEQUENCE: 46

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Tyr Ser Ser Leu Ala Trp Tyr Gln Gln Lys Pro Gly Gln Ala
    50                  55                  60

Pro Ser Leu Leu Ile Tyr Gly Ala Ser Ser Arg Ala Thr Gly Ile Pro
65                  70                  75                  80

Asp Arg Phe Ser Gly Ser Gly Ser Gly Pro Asp Phe Thr Leu Thr Ile
                85                  90                  95

Ser Arg Leu Glu Pro Glu Asp Phe Ala Val Tyr Tyr Cys Gln His Tyr
            100                 105                 110

Gly Asn Ser Pro Tyr Thr Phe Gly Gln Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 47
<211> LENGTH: 1407
<212> TYPE: DNA
<213> ORGANISM: Artificial
<220> FEATURE:
<223> OTHER INFORMATION: DNA sequence of PA-1 huMab Gamma heavy chain
      cDNA

<400> SEQUENCE: 47
atggactgga tctggaggat cctcttttg gtggcagcag ccacaggtgc ccactcccag       60
gtccagcttg tgcagtctgg ggctgaggtg aagaagcctg ggcctcagt gaaggtttcc      120 tgcaaggcct ctggatacac cttcactagc aatgctatac aatgggtgcg ccaggccccc     180
ggacaaaggc ttgagtgggt gggatggatc aacggtggcg atggtaacac aaaatattca     240
cagaagttcc agggcagagt caccattagt agggacatat ccgcgagcac agcctacatg     300
gagctgagca gcctgagatc tgaagacacg gctgtgtatt actgtgcgag acatcgtttg     360
caaagagggg ggttcgaccc ctggggccag ggaaccctgg tcaccgtctc ctcagcctcc     420
accaagggcc catcggtctt ccccctggca ccttcctcca agagcacctc tgggggcaca     480
gcggccctgg gctgcctggt caaggactac ttccccgaac cggtgacggt gtcgtggaac     540

```
tcaggcgccc tgaccagcgg cgtgcacacc ttcccggctg tcctacagtc ctcaggactc    600
tactccctca gcagcgtggt gaccgtgccc tccagcagct gggcaccca gacctacatc    660 tgcaacgtga atcacaagcc cagcaacacc aaggtggaca agagagttga gcccaaatct    720
tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca agccgcggg aggagcagta caacagcacg    960
taccgtgtgg tcagcgtcct caccgtcctg caccaggact ggctgaatgg caaggagtac    1020
aagtgcaagg tctccaacaa agccctccca gcccccatcg agaaaaccat ctccaaagcc    1080
aaagggcagc cccgagaacc acaggtgtac accctgcccc catcccggga ggagatgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttcct ctatagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaatga                                       1407
```

<210> SEQ ID NO 48
<211> LENGTH: 468
<212> TYPE: PRT
<213> ORGANISM: Artificial
<220> FEATURE:
<223> OTHER INFORMATION: Amino acid sequence of PA-1 huMab Gamma heavy
      chain

<400> SEQUENCE: 48

Met Asp Trp Ile Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Asn Ala Ile Gln Trp Val Arg Gln Ala Pro Gly Gln Arg Leu
    50                  55                  60

Glu Trp Val Gly Trp Ile Asn Gly Gly Asp Gly Asn Thr Lys Tyr Ser
65                  70                  75                  80

Gln Lys Phe Gln Gly Arg Val Thr Ile Ser Arg Asp Ile Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg His Arg Leu Gln Arg Gly Gly Phe Asp Pro Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

| | | | | | | | | | | | |
|---|---|---|---|---|---|---|---|---|---|---|---|
|Val|Pro|Ser|Ser|Ser|Leu|Gly|Thr|Gln|Thr|Tyr|Ile|Cys|Asn|Val|Asn|
| |210| | | | |215| | | | |220| | | | |

His Lys Pro Ser Asn Thr Lys Val Asp Lys Arg Val Glu Pro Lys Ser
225             230             235             240

Cys Asp Lys Thr His Thr Cys Pro Pro Cys Pro Ala Pro Glu Leu Leu
            245             250             255

Gly Gly Pro Ser Val Phe Leu Phe Pro Pro Lys Pro Lys Asp Thr Leu
            260             265             270

Met Ile Ser Arg Thr Pro Glu Val Thr Cys Val Val Val Asp Val Ser
        275             280             285

His Glu Asp Pro Glu Val Lys Phe Asn Trp Tyr Val Asp Gly Val Glu
    290             295             300

Val His Asn Ala Lys Thr Lys Pro Arg Glu Glu Gln Tyr Asn Ser Thr
305             310             315             320

Tyr Arg Val Val Ser Val Leu Thr Val Leu His Gln Asp Trp Leu Asn
            325             330             335

Gly Lys Glu Tyr Lys Cys Lys Val Ser Asn Lys Ala Leu Pro Ala Pro
            340             345             350

Ile Glu Lys Thr Ile Ser Lys Ala Lys Gly Gln Pro Arg Glu Pro Gln
        355             360             365

Val Tyr Thr Leu Pro Pro Ser Arg Glu Glu Met Thr Lys Asn Gln Val
    370             375             380

Ser Leu Thr Cys Leu Val Lys Gly Phe Tyr Pro Ser Asp Ile Ala Val
385             390             395             400

Glu Trp Glu Ser Asn Gly Gln Pro Glu Asn Asn Tyr Lys Thr Thr Pro
            405             410             415

Pro Val Leu Asp Ser Asp Gly Ser Phe Phe Leu Tyr Ser Lys Leu Thr
            420             425             430

Val Asp Lys Ser Arg Trp Gln Gln Gly Asn Val Phe Ser Cys Ser Val
        435             440             445

Met His Glu Ala Leu His Asn His Tyr Thr Gln Lys Ser Leu Ser Leu
    450             455             460

Ser Pro Gly Lys
465

```
<210> SEQ ID NO 49
<211> LENGTH: 702
<212> TYPE: DNA
<213> ORGANISM: Artificial
<220> FEATURE:
<223> OTHER INFORMATION: DNA sequence of LF-1 hubMab Kappa light chain
      cDNA

<400> SEQUENCE: 49
atgttgccat cacaactcat tgggtttctg ctgctctggg ttccagcctc caggggtgaa      60
attgtgctga ctcagtctcc agactttcag tctgtgagtc aaaggagaa agtcaccatc     120 acctgccggg ccagccagag cgttggtagt agcttacact ggtaccagca gaaaccagat    180
cagtctccaa agctcctcat caagtatgct tcccagtcct tctcaggggt ccctcgagg     240 ttcagtggca gtggatctgg gacagatttc accctcacca tcaatagcct ggaaactgaa    300
gatgctgcaa cgtattactg tcatcagagt agtagtttac ctctcacttt cggcggaggg    360
accaaggtgg agatcaaacg aactgtggct gcaccatctg tcttcatctt cccgccatct    420
gatgagcagt tgaaatctgg aactgcctct gttgtgtgcc tgctgaataa cttctatccc    480
```

```
agagaggcca aagtacagtg gaaggtggat aacgccctcc aatcgggtaa ctcccaggag    540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgtt ag                      702
```

<210> SEQ ID NO 50
<211> LENGTH: 233
<212> TYPE: PRT
<213> ORGANISM: Artificial
<220> FEATURE:
<223> OTHER INFORMATION: Amino acid sequence of LF-1 huMab Kappa light
      chain

<400> SEQUENCE: 50

```
Met Leu Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Ser Pro Lys Glu Lys Val Thr Ile Thr Cys Arg Ala Ser Gln Ser Val
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Thr Glu Asp Ala Ala Thr Tyr Tyr Cys His Gln Ser Ser Ser
            100                 105                 110

Leu Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 51
<211> LENGTH: 1413
<212> TYPE: DNA
<213> ORGANISM: Artificial
<220> FEATURE:
<223> OTHER INFORMATION: DNA sequence of LF-1 huMab Gamma heavy chain
      cDNA

<400> SEQUENCE: 51

```
atggagttgg ggctgtgctg gcttttcctt gtggctattt taaaaggtgt ccagtgtgag    60
gtgcagctgt tggagtctgg gggaggcttg gtacagccgg gggggtccct gagactctcc    120
```

```
tgttctggct ctggattcat gtttagcagt tatgccatga gctgggtccg ccaggctcca    180
gggaaggggc tggagtgggt ctcaggaatt agtggtagcg gtggtactac aaactacgca    240
gactccgtga agggccggtt caccatctcc agagacaatt ccaagaacac gctgtatatg    300
caaatgaaca gcctgagagc cgaggacacg gccgtatatt actgtgcgaa agatggggta    360
tatggccgac tggggggttc tgactactgg ggccagggaa ccctggtcac cgtctcctca    420
gcctccacca agggcccatc agtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgcccag cacctgaact cctggggggga   780
ccgtcagtct tcctcttccc cccaaaaccc aaggacaccc tcatgatctc ccggaccccct   840
gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag ggcagccccg agaaccacag gtgtacaccc tgcccccatc ccgggatgag   1140
ctgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg gtctgcacaa ccactacacg   1380
cagaagagcc tctccctgtc tccgggtaaa tga                                 1413
```

<210> SEQ ID NO 52  
<211> LENGTH: 470  
<212> TYPE: PRT  
<213> ORGANISM: Artificial  
<220> FEATURE:  
<223> OTHER INFORMATION: Amino acid sequence of LF-1 huMab Gamma heavy  
    chain

<400> SEQUENCE: 52

```
Met Glu Leu Gly Leu Cys Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ser Gly Ser Gly Phe Met Phe
        35                  40                  45

Ser Ser Tyr Ala Met Ser Trp Val Arg Gln Ala Pro Gly Lys Gly Leu
    50                  55                  60

Glu Trp Val Ser Gly Ile Ser Gly Ser Gly Gly Thr Thr Asn Tyr Ala
65                  70                  75                  80

Asp Ser Val Lys Gly Arg Phe Thr Ile Ser Arg Asp Asn Ser Lys Asn
                85                  90                  95

Thr Leu Tyr Met Gln Met Asn Ser Leu Arg Ala Glu Asp Thr Ala Val
            100                 105                 110

Tyr Tyr Cys Ala Lys Asp Gly Val Tyr Gly Arg Leu Gly Gly Ser Asp
        115                 120                 125
```

```
Tyr Trp Gly Gln Gly Thr Leu Val Thr Val Ser Ser Ala Ser Thr Lys
            130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Gly Leu His Asn His Tyr Thr Gln Lys Ser Leu
450                 455                 460

Ser Leu Ser Pro Gly Lys
465                 470
```

<210> SEQ ID NO 53
<211> LENGTH: 19
<212> TYPE: DNA
<213> ORGANISM: Artificial
<220> FEATURE:
<223> OTHER INFORMATION: oligonucleotides BamSfi 1

<400> SEQUENCE: 53
gatccggccc agccggccg                                              19

```
<210> SEQ ID NO 54
<211> LENGTH: 19
<212> TYPE: DNA
<213> ORGANISM: Artificial
<220> FEATURE:
<223> OTHER INFORMATION: oligonucleotides BamSfi 1

<400> SEQUENCE: 54
gatccggccg gctgggccg                                                  19

<210> SEQ ID NO 55
<211> LENGTH: 17
<212> TYPE: DNA
<213> ORGANISM: Artificial
<220> FEATURE:
<223> OTHER INFORMATION: oligonucleotides SacSfi 1

<400> SEQUENCE: 55
gcctcggggg ccgagct                                                    17

<210> SEQ ID NO 56
<211> LENGTH: 17
<212> TYPE: DNA
<213> ORGANISM: Artificial
<220> FEATURE:
<223> OTHER INFORMATION: oligonucleotides SacSfi 1

<400> SEQUENCE: 56
gcccccgagg ccgagct                                                    17

<210> SEQ ID NO 57
<211> LENGTH: 33
<212> TYPE: DNA
<213> ORGANISM: Artificial
<220> FEATURE:
<223> OTHER INFORMATION: mutant primer

<400> SEQUENCE: 57
ccgcgggagg agcagtacca aagcacgtac cgt                                  33

<210> SEQ ID NO 58
<211> LENGTH: 31
<212> TYPE: DNA
<213> ORGANISM: Artificial
<220> FEATURE:
<223> OTHER INFORMATION: reverse primer

<400> SEQUENCE: 58
gtactgctcc tcccgcggct ttgtcttggc a                                    31

<210> SEQ ID NO 59
<211> LENGTH: 12
<212> TYPE: PRT
<213> ORGANISM: Artificial
<220> FEATURE:
<223> OTHER INFORMATION: a light chain CDR1 with at least 90% sequence
      identity to PA-1CDR1:

<400> SEQUENCE: 59

Arg Ala Ser Gln Ser Val Ser Tyr Ser Ser Leu Ala
1               5                   10

<210> SEQ ID NO 60
<211> LENGTH: 7
<212> TYPE: PRT
<213> ORGANISM: Artificial
<220> FEATURE:
```

```
<223> OTHER INFORMATION: a light chain CDR2 with at least 90% sequence
      identity to PA-1CDR2

<400> SEQUENCE: 60

Gly Ala Ser Ser Arg Ala Thr
1               5

<210> SEQ ID NO 61
<211> LENGTH: 9
<212> TYPE: PRT
<213> ORGANISM: Artificial
<220> FEATURE:
<223> OTHER INFORMATION: a light chain CDR3 with at least 90% sequence
      identity to PA-1CDR3

<400> SEQUENCE: 61

Gln His Tyr Gly Asn Ser Pro Tyr Thr
1               5

<210> SEQ ID NO 62
<211> LENGTH: 10
<212> TYPE: PRT
<213> ORGANISM: Artificial
<220> FEATURE:
<223> OTHER INFORMATION: a heavy chain CDR1 with at least 90% sequence
      identity to PA-hCDR1

<400> SEQUENCE: 62

Gly Tyr Thr Phe Thr Ser Asn Ala Ile Gln
1               5                   10

<210> SEQ ID NO 63
<211> LENGTH: 17
<212> TYPE: PRT
<213> ORGANISM: Artificial
<220> FEATURE:
<223> OTHER INFORMATION: a heavy chain CDR2 with at least 90% sequence
      identity to PA-hCDR2

<400> SEQUENCE: 63

Trp Ile Asn Gly Gly Asp Gly Asn Thr Lys Tyr Ser Gln Lys Phe Gln
1               5                   10                  15

Gly

<210> SEQ ID NO 64
<211> LENGTH: 10
<212> TYPE: PRT
<213> ORGANISM: Artificial
<220> FEATURE:
<223> OTHER INFORMATION: a heavy chain CDR3 with at least 90% sequence
      identity to PA-hCDR3

<400> SEQUENCE: 64

His Arg Leu Gln Arg Gly Gly Phe Asp Pro
1               5                   10

<210> SEQ ID NO 65
<211> LENGTH: 11
<212> TYPE: PRT
<213> ORGANISM: Artificial
<220> FEATURE:
<223> OTHER INFORMATION: amino acid residues

<400> SEQUENCE: 65

Arg Ala Ser Gln Ser Val Gly Ser Ser Leu His
1               5                   10
```

```
<210> SEQ ID NO 66
<211> LENGTH: 7
<212> TYPE: PRT
<213> ORGANISM: Artificial
<220> FEATURE:
<223> OTHER INFORMATION: amino acid residues

<400> SEQUENCE: 66

Tyr Ala Ser Gln Ser Phe Ser
1               5

<210> SEQ ID NO 67
<211> LENGTH: 9
<212> TYPE: PRT
<213> ORGANISM: Artificial
<220> FEATURE:
<223> OTHER INFORMATION: amino acid residues

<400> SEQUENCE: 67

His Gln Ser Ser Ser Leu Pro Leu Thr
1               5

<210> SEQ ID NO 68
<211> LENGTH: 10
<212> TYPE: PRT
<213> ORGANISM: Artificial
<220> FEATURE:
<223> OTHER INFORMATION: amino acid residues

<400> SEQUENCE: 68

Gly Phe Met Phe Ser Ser Tyr Ala Met Ser
1               5                   10

<210> SEQ ID NO 69
<211> LENGTH: 17
<212> TYPE: PRT
<213> ORGANISM: Artificial
<220> FEATURE:
<223> OTHER INFORMATION: amino acid residues

<400> SEQUENCE: 69

Gly Ile Ser Gly Ser Gly Gly Thr Thr Asn Tyr Ala Asp Ser Val Lys
1               5                   10                  15
Gly

<210> SEQ ID NO 70
<211> LENGTH: 12
<212> TYPE: PRT
<213> ORGANISM: Artificial
<220> FEATURE:
<223> OTHER INFORMATION: amino acid residues

<400> SEQUENCE: 70

Asp Gly Val Tyr Gly Arg Leu Gly Gly Ser Asp Tyr
1               5                   10
```

COMPOSITIONS AND METHODS FOR PRODUCTION OF IMMUNOGLOBULINS

RELATED APPLICATIONS

This application claims priority to and the benefit of U.S. Provisional application No. 60/705,653, filed Aug. 3, 2005, the contents of which are hereby incorporated by reference in their entirety.

BACKGROUND OF THE INVENTION

Anthrax is a well-characterized infectious disease caused by the sporulating bacteria *Bacillus anthracis*. The disease is historically associated with animal infections, especially herbivores such as cows, sheep, and goats, and is not typically found in humans. However, humans working with animal products where infection occurs are at risk of contracting anthrax. Some regions of the Middle East and sub-Saharan Africa are hyperendemic for anthrax, though the organism can often be found in many areas of the world. The disease manifests in three different ways: cutaneous, gastrointestinal and inhalation anthrax result from exposure of an open wound to spores, ingesting spores in contaminated meat products, or inhaling spores, respectively. While cutaneous anthrax has a fatality rate of up to 25 percent, gastrointestinal or inhalation anthrax results in nearly 100 percent fatalities. Definitive diagnosis of anthrax infection often comes too late to provide resuscitative care.

The principal virulence factor of *B. anthracis* is a multi-component toxin secreted by the organism. The toxin consists of three proteins designated protective antigen (PA), lethal factor (LF) and edema factor (EF), which are encoded by the genes pag, lef, and cya, respectively. PA is a 735 amino acid protein of molecular weight 83 kDa. It binds to the anthrax toxin receptor (ATR) on a mammalian cell surface, and subsequently undergoes a furin-mediated cleavage to yield a 63 kDa receptor-bound product. The 63 kDa PA fragment forms a heptameric complex on the cell surface which is capable of interacting with either LF or EF, and this complex is subsequently internalized. LF is a zinc metalloprotease that cleaves several isoforms of MAP kinase, thereby disrupting signal transduction events within a cell, eventually leading to cell death. LF is considered responsible for the lethal outcome of anthrax infection. EF is a calmodulin-dependent adenylate cyclase that causes deregulation of cellular physiology, leading to clinical manifestations that include edema. PA and LF together are referred to as lethal toxin.

The CDC lists anthrax as a category A disease agent and estimates the cost of an anthrax attack to exceed $26 billion per 100,000 persons exposed. Presently, the only vaccine licensed for human use in the U.S., Biothrax (formerly Anthrax vaccine adsorbed, or AVA), is an aluminum hydroxide-adsorbed, formalin-treated subunit vaccine based on protective antigen, PA. It is delivered by subcutaneous injection and induces immunity against lethal toxin secreted by the bacillus. The vaccine is produced from the filtered culture supernatant fraction of the V770-NP1-R strain of *B. anthracis*. The production process is complex, there is variation from batch-to-batch in vaccine preparation lots, and the precise composition of the vaccine is undetermined. Furthermore, since alum is included as an adjuvant with the current vaccine, a cold chain must be maintained during vaccine storage and distribution, adding inconvenience and cost. The vaccine is administered by injection, which can complicate the logistics of mass treatments. Thus, it would be desirable to have additional reagents capable of countering the infectious potential of an anthrax outbreak or attack.

Monoclonal antibodies are of increasing importance for a variety of therapeutic as well as diagnostic, industrial, and research purposes. For example, several animal studies have demonstrated anthrax toxin-specific antibodies from vaccinated animals can passively protect recipients from lethal effects of infection. However, animal-derived sera has obvious drawbacks which prevent widespread use as therapeutics. Monoclonal antibodies produced by hybridomas must be harvested from medium in which the hybridomas are cultured or harvested from mouse ascites fluid. Unfortunately, these production systems are expensive, labor-intensive, and have other significant disadvantages. For these reasons and others it would be desirable to be able to utilize alternative production systems for monoclonal antibodies such as production systems involving recombinant DNA technology.

Concerns regarding sufficient access and limited supply of reagents, product cost, and reagent purity underscore the urgent need for improved products and reagents. Thus, there exists a clear need and urgency for improved approaches to counter potential anthrax infection, as well as for improved methods of diagnostic detection, and research tools useful in examination of anthrax infection mechanism. Furthermore, it is desirable to provide production methods that allow for mass-production of products useful in such applications at reasonable cost.

SUMMARY OF THE INVENTION

The present invention provides nucleic acid and protein sequences useful in the preparation of antibodies in recombinant systems. In particular, provided are oligonucleotide primer sequences useful for preparation of nucleic acid sequences encoding a light chain antibody sequence and a heavy chain antibody sequence. Additionally provided are an antibody nucleic acid sequence encoding a polypeptide consisting of at least one heavy chain polypeptide or functional fragment thereof; and an antibody nucleic acid sequence encoding at least one light chain polypeptide or functional fragment thereof. Also provided are heavy and light chain polypeptides and functional fragment(s) thereof. The invention additionally provides antibody sequences of PA-1 and LF-1 antibodies each independently comprising at least one CDR heavy chain polypeptide and at least one CDR light chain polypeptide. Also provided are antibody sequences of PA-1 and LF-1 antibodies each independently comprising one or more CDRs having at least one amino acid substitution, where the PA-1 or LF-1 binding activity is enhanced. Nucleic acids encoding PA-1 and LF-1 heavy and light chains as well as nucleic acids encoding PA-1 and LF-1 antibodies are additionally provided. Functional fragments of such encoding nucleic acids are similarly provided. Methods of production and use of provided compositions are also provided herein.

DEFINITIONS

Figure 1:
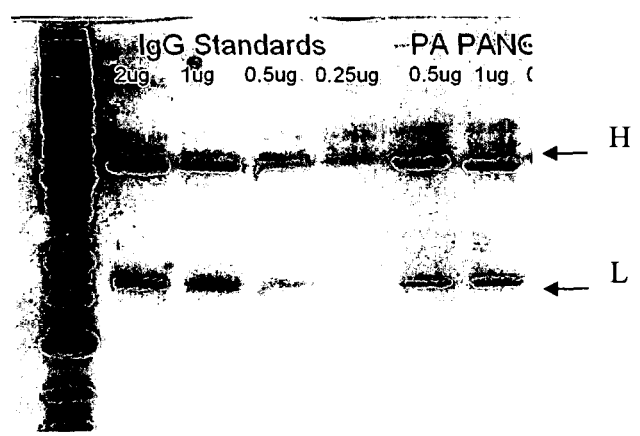
FIG. 1 is a photograph of a gel showing SDS-PAGE analysis of PA and PANG (nonglycosylated) plant-produced antibodies. IgG standards are purified total human IgG. Positions of the heavy (H) and light (L) chains are indicated by arrows.
Figure 2:
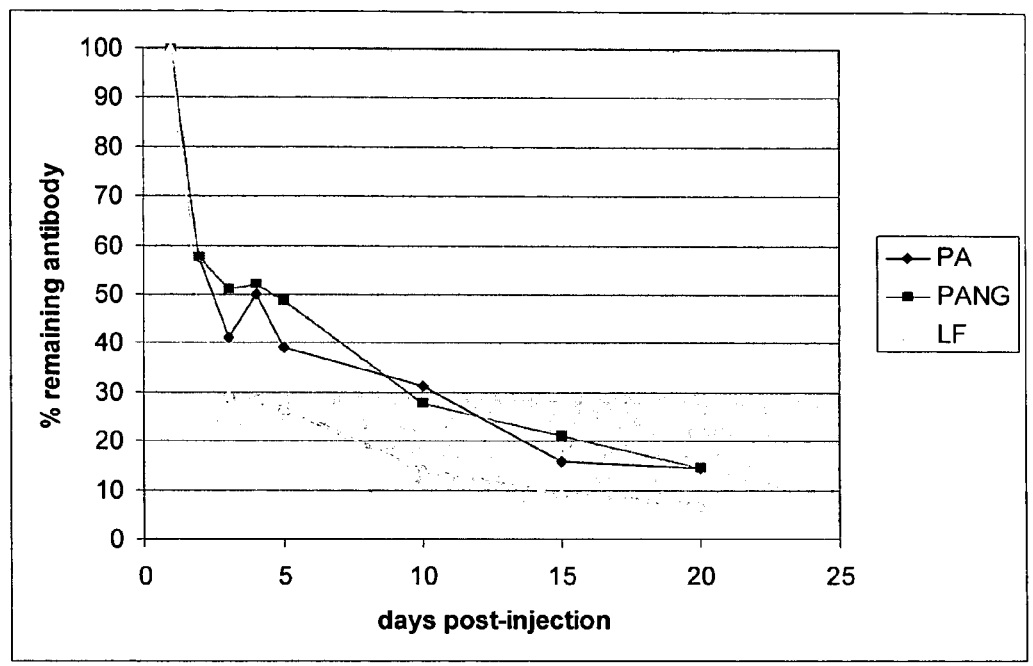
FIG. 2 is a graph depicts results of rat half life studies of plant produced PA (PA), or PANG (PANG), LF (LF) antibody.

The terms "antibody", "antibody chain", "variable region or domain", "constant region or domain", "gamma chain", "kappa chain", "lambda chain", "heavy chain", "light chain", and other terms relevant to antibodies are used herein in accordance with their art-accepted meanings as described, e.g., in Goldby, R. A., *Kuby Immunology*, supra, and/or Harlow, supra.

The term "cDNA" refers to a single-stranded DNA molecule that is complementary to an mRNA or to a double-stranded DNA molecule that comprises a strand that is complementary to an mRNA. The other strand of the double-stranded cDNA will have the same sequence as the mRNA and will thus encode the same polypeptide as the mRNA.

An "expression vector" is a vector that contains regulatory sequences (e.g., promoters and/or other expression signals and, optionally, 3' sequences, such as 3' regulatory sequences or termination signals sufficient to drive transcription of a nucleic acid segment to which they are operably linked. The expression vector may also comprise operably linked sequences required for proper translation of the nucleic acid segment. The nucleic acid segment may, but need not be, a protein coding sequence. The nucleic acid segment may be chimeric, meaning that it includes more than one sequence of distinct origin that are joined together by recombinant DNA techniques, resulting in a nucleotide sequence that does not occur naturally. The term "expression vector" can refer to a vector either before or after insertion of the operably linked nucleic acid segment. Certain expression vectors allow the shuttling of DNA between hosts such as bacteria-yeast, or bacteria-animal cells, or bacteria-fungal cells, or bacteria-invertebrate cells, or bacteria-plant cells. A typical expression vector will contain an origin of replication for autonomous replication in host cells, one or more selectable markers, one or more (typically several) useful restriction enzyme sites, frequently a potential for high copy number, and one or more promoters.

"Identity" refers to the extent to which the sequence of two or more nucleic acids is the same. The percent identity between first and second nucleic acids over a window of evaluation may be computed by aligning the nucleic acids, determining the number of nucleotides within the window of evaluation that are opposite an identical nucleotide allowing the introduction of gaps to maximize identity, dividing by the total number of nucleotides in the window, and multiplying by 100. When computing the number of identical nucleotides needed to achieve a particular % identity, fractions are to be rounded to the nearest whole number. When two or more sequences are compared, any of them may be considered the reference sequence.

Percent identity can be calculated using a variety of computer programs known in the art. For example, computer programs such as BLASTN, BLASTP, Gapped BLAST, etc., generate alignments and provide % identity between a sequence of interest and sequences in any of a variety of public databases. The algorithm of Karlin and Altschul (Karlin and Altschul, *Proc. Natl. Acad. Sci. USA* 87:22264-2268, 1990) modified as in Karlin and Altschul, *Proc. Natl. Acad. Sci. USA* 90:5873-5877, 1993 is incorporated into the NBLAST and XBLAST programs of Altschul et al. (Altschul, et al., *J. Mol. Biol.* 215:403-410, 1990). To obtain gapped alignments for comparison purposes, Gapped BLAST is utilized as described in Altschul et al. (Altschul, et al. *Nucleic Acids Res.* 25: 3389-3402, 1997). When utilizing BLAST and Gapped BLAST programs, the default parameters of the respective programs are used. See the World Wide Web site having URL ncbi.nlm.nih.gov. A PAM250 or BLOSUM62 matrix may be used.

The term "isolated" means 1) separated from at least some of the components with which it is usually associated in nature; 2) prepared or purified by a process that involves the hand of man; and/or 3) not occurring in nature. A nucleic acid that is excised from or amplified from a larger nucleic acid (e.g., a chromosome, episome, viral or bacterial genome) in which it is naturally found is considered isolated. In some embodiments the excised or amplified nucleic acid is no longer joined to non-coding regions (but may be joined to its native regulatory regions or portions thereof), or to other genes, which are located upstream or downstream from the isolated nucleic acid as found in the larger nucleic acid. Isolated nucleic acids include nucleic acids inserted into plasmids, cosmids, artificial chromosomes, viral vectors, and the like, i.e., a nucleic acid that forms part of a recombinant nucleic acid construct is considered isolated. An isolated nucleic acid can be an amplification product (e.g., a PCR product), an isolated mRNA, a cDNA, a restriction fragment, etc. An isolated polypeptide can be a polypeptide expressed in a heterologous expression system, i.e., expressed by a cell that does not express the polypeptide in nature. An isolated antibody can be an antibody that is present in a composition other than blood or serum. An antibody that is expressed from an isolated nucleic acid is considered to be an isolated antibody. Any of the nucleic acids, antibody chains, or antibodies of the invention can be provided in isolated form.

The terms "nucleic acid", "polynucleotide", and "oligonucleotide" are used interchangeably herein to refer to a polymer of at least three nucleotides. A nucleoside comprises a nitrogenous base linked to a sugar molecule. In a polynucleotide, phosphate groups covalently link adjacent nucleosides to form a polymer. The polymer may include natural nucleosides (e.g., adenosine, thymidine, guanosine, cytidine, uridine, deoxyadenosine, deoxythymidine, deoxyguanosine, and deoxycytidine), nucleoside analogs, chemically modified bases, biologically modified bases (e.g., methylated bases), intercalated bases, modified sugars (e.g, modified purines or pyrimidines). See Kornberg and Baker, *DNA Replication*, 2nd Ed. (Freeman, San Francisco, 1992), Scheit, *Nucleotide Analogs* (John Wiley, New York, 1980), and U.S. Patent Publication No. 20040092470 and references therein for further discussion of various nucleotides, nucleosides, and backbone structures that can be used in the polynucleotides described herein, and methods for producing them. Analogs such as peptide nucleic acids, locked nucleic acids, etc., are also within the scope of the invention. A polynucleotide may be of any size or sequence and may be single- or double-stranded. An oligonucleotide is typically less than 100 nucleotides in length. Any nucleic acid disclosed herein can be in single or double-stranded form. Where the invention provides a nucleic acid sequence, the complementary sequence is also provided. Furthermore, where a sequence is provided as DNA, the corresponding RNA sequence (i.e., the sequence in which T is replaced by U, is also provided).

The term "nucleic acid construct" is used to refer to a nucleic acid that has been modified by the hand of man or is derived from such a nucleic acid. For example, a nucleic acid construct can contain a mutation, deletion, or substitution relative to a naturally occurring nucleic acid molecule. A nucleic acid construct can comprise two or more nucleic acid segments that are derived from or originate from different sources such as different organisms, e.g., a recombinant polynucleotide. The sequence of one or more portions of a nucleic acid construct may be entirely invented by man.

The term "nucleic acid sequence" as used herein can refer to the nucleic acid material itself and is not restricted to the sequence information (i.e. the succession of letters chosen among the five base letters A, G, C, T, or U) that biochemically characterizes a specific nucleic acid, e.g., a DNA or RNA molecule.

"Operably linked" or "operably associated" refers to a functional relationship between two nucleic acids, wherein the expression, activity, localization, etc., of one of the sequences is controlled by, directed by, regulated by, modulated by, etc., the other nucleic acid. The two nucleic acids are said to be operably linked or operably associated. "Operably linked" or "operably associated" also refers to a relationship between two polypeptides wherein the expression of one of the polypeptides is controlled by, directed by, regulated by, modulated by, etc., the other polypeptide. The two nucleic acids are said to be operably linked or operably associated. For example, transcription of a nucleic acid is directed by an operably linked promoter; post-transcriptional processing of a nucleic acid is directed by an operably linked processing sequence; translation of a nucleic acid is directed by an operably linked translational regulatory sequence such as a translation initiation sequence; transport, stability, or localization of a nucleic acid or polypeptide is directed by an operably linked transport or localization sequence such as a secretion signal sequence; and post-translational processing of a polypeptide is directed by an operably linked processing sequence. Preferably a first nucleic acid sequence that is operably linked to a second nucleic acid sequence, or a first polypeptide that is operatively linked to a second polypeptide, is covalently linked, either directly or indirectly, to such a sequence, although any effective three-dimensional association is acceptable. One of ordinary skill in the art will appreciate that multiple nucleic acids, or multiple polypeptides, may be operably linked or associated.

The term "primer" refers to a single-stranded oligonucleotide which acts as a point of initiation of template-directed DNA synthesis under appropriate conditions (e.g., in the presence of four different nucleoside triphosphates and a polymerization agent, such as DNA polymerase, RNA polymerase or reverse transcriptase) in an appropriate buffer solution containing any necessary cofactors and at a suitable temperature. The appropriate length of a primer depends on the intended use of the primer, but typically ranges from approximately 10 to approximately 50 nucleotides. A primer need not be perfectly complementary to the template but should be sufficiently complementary to hybridize with it. A primer can be provided in double-stranded form, i.e., hybridized to its complement.

"Purified", as used herein, means that an entity or substance is separated from one or more other entities or substances with which it was previously found before being purified. An entity or substance may be partially purified, substantially purified, or pure. A substance or entity such as a nucleic acid or polypeptide is considered pure when it is removed from substantially all other compounds or entities other than a solvent and any ions contained in the solvent, i.e., it constitutes at least about 90%, more preferably at least about 91%, 92%, 93%, 94%, 95%, 96%, 97%, 98%, 99%, or greater than 99% of the dry weight of the composition. A partially or substantially purified compound or entity such as a nucleic acid or polypeptide may be removed from at least 50%, at least 60%, at least 70%, or at least 80% of the material with which it is naturally found, e.g., cellular material such as cellular proteins and/or nucleic acids. In certain embodiments the of a purified nucleic acid or polypeptide constitutes at least 10%, 20%, 30%, 40%, 50%, 60%, 70%, 80%, 90%, 95%, 99% or even more, by dry weight, of the total nucleic acid or polypeptide, respectively, in a composition. Methods for assessing purity are known in the art and include chromatographic methods, immunological methods, electrophoretic methods, etc.

The term "regulatory element" or "regulatory sequence" in reference to a nucleic acid is generally used herein to describe a portion of nucleic acid that directs or controls one or more steps in the expression (particularly transcription, but in some cases other events such as splicing or other processing) of nucleic acid sequence(s) with which it is operatively linked. The term includes promoters and can also refer to enhancers, silencers, and other transcriptional control elements. Promoters are regions of nucleic acid that include a site to which RNA polymerase binds before initiating transcription and that are typically necessary for even basal levels of transcription to occur. Generally such elements comprise a TATA box. Enhancers are regions of nucleic acid that encompass binding sites for protein(s) that elevate transcriptional activity of a nearby or distantly located promoter, typically above some basal level of expression that would exist in the absence of the enhancer. In some embodiments of the invention, regulatory sequences may direct constitutive expression of a nucleotide sequence, e.g., expression may occur in most or all cell types and/or under most or all conditions; in other embodiments, regulatory sequences may direct cell or tissue-specific and/or inducible expression. For example, expression may be induced by the presence or addition of an inducing agent such as a hormone or other small molecule, by an increase in temperature, etc. Regulatory elements may also inhibit or decrease expression of an operatively linked nucleic acid. Regulatory elements that behave in this manner will be referred to herein as "negative regulatory elements.

In general, the level of expression may be determined using standard techniques for measuring mRNA or protein. Such methods include Northern blotting, in situ hybridization, RT-PCR, sequencing, immunological methods such as immunoblotting, immunodetection, or fluorescence detection following staining with fluorescently labeled antibodies, oligonucleotide or cDNA microarray or membrane array, protein array analysis, mass spectrometry, etc. A convenient way to determine expression level is to place a nucleic acid that encodes a readily detectable marker (e.g., a fluorescent or luminescent protein such as green fluorescent protein or luciferase, an enzyme such as alkaline phosphatase, etc.) in operable association with the regulatory element in an expression vector, introduce the vector into a cell type of interest or into an organism, maintain the cell or organism for a period of time, and then measure expression of the readily detectable marker, taking advantage of whatever property renders it readily detectable (e.g., fluorescence, luminescence, alteration of optical property of a substrate, etc.). Comparing expression in the absence and presence of the regulatory element indicates the degree to which the regulatory element affects expression of an operatively linked sequence.

"Specific binding" generally refers to a physical association between a target polypeptide (or, more generally, a target molecule) and a binding molecule such as an antibody or ligand. The association is typically dependent upon the presence of a particular structural feature of the target such as an antigenic determinant or epitope recognized by the binding molecule. For example, if an antibody is specific for epitope A, the presence of a polypeptide containing epitope A or the presence of free unlabeled A in a reaction containing both free labeled A and the binding molecule that binds thereto, will reduce the amount of labeled A that binds to the binding molecule. It is to be understood that specificity need not be absolute but generally refers to the context in which the binding occurs. For example, it is well known in the art that numerous antibodies cross-react with other epitopes in addition to those present in the target molecule. Such cross-reactivity may be acceptable depending upon the application for which the antibody is to be used. One of ordinary skill in the art will be able to select antibodies or ligands having a sufficient degree of specificity to perform appropriately in any given application (e.g., for detection of a target molecule, for therapeutic purposes, etc). It is also to be understood that specificity may be evaluated in the context of additional factors such as the affinity of the binding molecule for the target versus the affinity of the binding molecule for other targets, e.g., competitors. If a binding molecule exhibits a high affinity for a target molecule that it is desired to detect and low affinity for nontarget molecules, the antibody will likely be an acceptable reagent. Once the specificity of a binding molecule is established in one or more contexts, it may be employed in other, preferably similar, contexts without necessarily re-evaluating its specificity. Binding of two or more molecules may be considered specific if the affinity (equilibrium dissociation constant, Kd) is at least $10^{-3}$ M, preferably $10^{-4}$ M, more preferably $10^{-5}$ M, e.g., $10^{-6}$ M, $10^{-7}$ M, $10^{-8}$ M, or $10^{-9}$ M under the conditions tested, e.g., under physiological conditions.

"Subject", as used herein, refers to an individual to whom an antibody composition is to be delivered, e.g., for experimental, diagnostic, and/or therapeutic purposes. Preferred subjects are mammals, particularly domesticated mammals (e.g., dogs, cats, etc.), primates, or humans.

"Treating", as used herein, can generally include reversing, alleviating, reducing, inhibiting the progression of, or reducing the likelihood of the disease, disorder, or condition to which such term applies, or one or more symptoms or manifestations of such disease, disorder or condition. "Preventing" refers to causing a disease, disorder, condition, or symptom or manifestation of such, or worsening of the severity of such, not to occur.

"Vector" is used herein to refer to a nucleic acid or a virus, viral genome, or portion thereof (e.g., a viral capsid or a component of a viral genome) capable of mediating entry of, e.g., transferring, transporting, etc., a nucleic acid molecule into a cell. Where the vector is a nucleic acid, the nucleic acid molecule to be transferred is generally linked to, e.g., inserted into, the vector nucleic acid molecule. A nucleic acid vector may include sequences that direct autonomous replication within suitable host cells (e.g., an origin of replication), or may include sequences sufficient to allow integration of part of all of the nucleic acid into host cell DNA. Useful nucleic acid vectors include, for example, DNA or RNA plasmids, cosmids, and naturally occurring or modified viral genomes or portions thereof or nucleic acids (DNA or RNA) that can be packaged into viral capsids. Plasmid vectors typically include an origin of replication and one or more selectable markers. Plasmids may include part or all of a viral genome (e.g., a viral promoter, enhancer, processing or packaging signals, etc.). Viruses or portions thereof (e.g., viral capsids) that can be used to introduce nucleic acid molecules into cells are referred to as viral vectors. Useful animal viral vectors include adenoviruses, retroviruses, lentiviruses, vaccinia virus and other poxviruses, herpex simplex virus, and others. Useful plant viral vectors include those based on tobamoviruses, ilarviruses, etc. Viral vectors may or may not contain sufficient viral genetic information for production of infectious virus when introduced into host cells, i.e., viral vectors may be replication-defective, and such replication-defective viral vectors may be preferable for certain embodiments of the invention. Where sufficient information is lacking it may, but need not be, supplied by a host cell or by another vector introduced into the cell.

DETAILED DESCRIPTION OF CERTAIN EMBODIMENTS OF THE INVENTION

The invention is directed to nucleic acids encoding the monoclonal antibody (MAb) PA, and nucleic acids encoding the monoclonal antibody LF. Antibodies encoded by the nucleic acids, and functional fragments thereof, specifically recognize the anthrax proteins PA and LF, respectively, and inhibit activity, and productive anthrax infection. The invention is also directed to nucleic acids encoding and to polypeptides comprising modified forms of PA and/or LF, and functional fragments thereof. These antibodies and functional fragments retain the binding specificity and inhibitory activity of the parent murine antibody PA and/or LF. The invention is additionally directed to optimized forms of PA and/or LF antibodies that exhibit increased binding affinity and specificity compared to the parental forms of the PA and/or LF antibody.

The hybridoma method, first described by Kohler & Milstein, *Nature* 256: 495, 1975, is widely used for the identification of monoclonal antibodies that exhibit desired binding properties. Briefly, the technique generally involves isolating lymphocytes from an immunized mammal, fusing the lymphocytes with myeloma cells, and isolating clonal cell lines (hybridomas) generated from the fusion. These cell lines are screened to identify those that produce an antibody that binds to the polypeptide of interest or to a particular portion or antigenic determinant thereof. Lines can also be screened to identify ones that produce an antibody having a desired affinity for the target polypeptide. The immunized mammal may have been deliberately immunized, e.g., vaccinated, or may have been infected by an infectious organism, exposed to an antigen, etc. Thus an "immunized mammal" refers to any mammal that produces an antibody that specifically binds to a polypeptide of interest. In a preferred embodiment of the present invention the mammal is a human being, e.g., a human being who has been vaccinated against an infectious agent, exposed to an infectious agent, etc.

The present invention provides oligonucleotide primers and primer sets for use in isolating cDNAs that encode antibody heavy or light chains from hybridomas, e.g., using polymerase chain reaction (PCR).

In one embodiment, an oligonucleotide comprises any of SEQ ID NOs: 1-44. In another embodiment, an oligonucleotide consists of any of SEQ ID NOs: 1-44. In other aspects, the restriction enzyme site provided in certain primers may be modified to any preferred restriction enzyme site, in order to adapt the primers to desirable vector insert sites.

In another aspect, the invention provides a method of isolating a nucleic acid that encodes an antibody chain or portion thereof. In one embodiment, the method comprises the steps of: (a) contacting nucleic acids obtained from an antibody-producing cell with at least one oligonucleotide primer selected from the group consisting of SEQ ID NOs: 1-44; and (b) performing an amplification reaction. The amplification reaction is typically a polymerase chain reaction (PCR). In certain embodiments of the invention step (a) comprises containct the nucleic acids with at least two oligonucleotide primers selected from the group consisting of SEQ ID NOs: 1-44. It will be appreciated that while the primers and methods of the present invention may have particular use for cloning antibody chain cDNAs (i.e., cDNAs that encode an antibody chain) from hybridomas, they are in no way limited to that purpose but can be used for cloning antibody chain cDNAs from any antibody producing cell, cell line, etc. Preferably the antibody chain is a human antibody chain.

In another aspect, the invention provides nucleic acid compositions encoding antibody polypeptide chains, or functional fragments thereof which bind an anthrax protein. In one embodiment, nucleic acid compositions encoding antibody polypeptide chain or a functional fragment thereof comprise a functional protein which binds *B. anthracis* protective antigen. In one embodiment provided is a nucleic acid that encodes a kappa light chain of a monoclonal antibody, or a functional fragment thereof, that binds to *B. anthracis* protective antigen. In one embodiment the nucleic acid is or comprises the sequence of a cDNA. In another embodiment, provided is a nucleic acid that encodes a gamma heavy chain of a monoclonal antibody, or a functional fragment thereof, that binds to *B. anthracis* protective antigen. In one embodiment the nucleic acid is or comprises the sequence of a cDNA.

In one embodiment, nucleic acid compositions encoding antibody polypeptide chain or a functional fragment thereof comprise a functional protein which binds *B. anthracis* lethal factor. In one embodiment, provided is a nucleic acid that encodes a kappa light chain of a monoclonal antibody, or a functional fragment thereof, that binds to *B. anthracis* lethal factor. In one embodiment the nucleic acid is or comprises the sequence of a cDNA. In another embodiment, provided is a nucleic acid that encodes a gamma heavy chain of a monoclonal antibody, or a functional fragment thereof, that binds to *B. anthracis* lethal factor. In one embodiment the nucleic acid is or comprises the sequence of a cDNA.

Further provided is a variety of nucleic acid constructs comprising one or more inventive nucleic acids, e.g., a nucleic acid that encodes an antibody heavy chain or light chain, wherein said nucleic acid was isolated from a cell or cell line that expresses the antibody heavy or light chain using one or more of the inventive primers. For example, the invention provides vectors, e.g., expression vectors, containing one or more inventive nucleic acids. In certain embodiments a vector is a binary vector suitable for *Agrobacterium*-mediated transformation. In certain embodiments a vector is a plant virus. In certain embodiments a vector is based on a plant virus, i.e., it contains one or more genomic components of a plant virus.

The invention further provides host cells that express one or more of provided nucleic acids and produce a heavy or light chain of a monoclonal antibody, or functional fragments thereof.

The invention further provides a method of producing an antibody heavy or light chain comprising: (i) providing an expression system that contains a nucleic acid that encodes a heavy or light chain of a monoclonal antibody, or a functional fragment thereof, wherein said nucleic acid was isolated using one or more primers of the invention, wherein said nucleic acid is operably linked to a regulatory element such as a promoter that directs expression of the nucleic acid in the expression system; (ii) maintaining the expression system under conditions in which expression occurs. The method may further comprise (iii) harvesting the antibody, or functional fragment thereof. The antibody or functional fragment thereof may be purified using any of a variety of techniques known in the art. The expression system can be any suitable expression system, e.g., a cell culture, transgenic plant or animal, clonal root or plant line, etc. A complete antibody can be produced by allowing the heavy and light chains to associate with one another.

The invention further provides a method of producing antibody comprising a heavy chain and a light chain, or functional fragments thereof comprising: (i) providing an expression system that contains a nucleic acid that encodes an antibody heavy chain or functional fragment thereof and further contains a nucleic acid that encodes an antibody light chain or functional fragment thereof, wherein either or both of said nucleic acids was isolated using one or more primers of the present invention, and wherein each of said nucleic acids is operably linked to a regulatory element such as a promoter that directs expression in the expression system; (ii) maintaining the expression system under conditions in which expression occurs. The antibody chains are both produced by the expression system and can associate with one another in the expression system. The method may further include a step of harvesting the antibody. Any suitable expression system can be used.

The invention further provides a method of treating a subject comprising administering an antibody comprising a heavy and light chain, or functional fragments thereof, wherein either or both chains were produced according to an inventive method described herein.

This application refers to various patents, patent applications, journal articles, and other publications, all of which are incorporated herein by reference. In addition, the following standard reference works are incorporated herein by reference: Ausubel, F., (ed.), *Current Protocols in Molecular Biology, Current Protocols in Immunology, Current Protocols in Protein Science*, and *Current Protocols in Cell Biology*, John Wiley & Sons, N.Y., edition as of July 2002; Sambrook, Russell, and Sambrook, *Molecular Cloning: A Laboratory Manual*, 3$^{rd}$ ed., Cold Spring Harbor Laboratory Press, Cold Spring Harbor, 2001; Harlow, E., et al., *Antibodies: A Laboratory Manual,* (Cold Spring Harbor Laboratory Press, 2nd ed. 1988); Goldsby, R. A., et al., (eds.), *Kuby Immunology,* 4$^{th}$ ed., W.H. Freeman & Company, New York, 2000; and *Goodman and Gilman's The Pharmacological Basis of Therapeutics*, 10$^{th}$ Ed. McGraw Hill, 2001. In the event of a conflict or inconsistency between any of the incorporated references and the instant specification or the understanding of one or ordinary skill in the art, the specification shall control, it being understood that the determination of whether a conflict or inconsistency exists is within the discretion of the inventors and can be made at any time.

The present invention provides novel oligonucleotide primers and primer sets for use in isolating nucleic acids, e.g., cDNAs, that encode antibody heavy or light chains from hybridomas, e.g., using the polymerase chain reaction (PCR). PCR is well known in the art and is described, e.g., in *PCR Primer: A Laboratory Manual*, Dieffenbach, C. W. and Dveksler, G. S. (Eds.); *PCR Basics: From Background to Bench*, Springer Verlag, 2000; M. J. McPherson, et al; Mattila et al., *Nucleic Acids Res.,* 19:4967 (1991); Eckert et al., PCR Methods and Applications, 1:17 (1991); PCR (eds. McPherson et al., IRL Press, Oxford); and U.S. Pat. No. 4,683,202. In certain embodiments of the invention RNA, e.g., mRNA, is isolated from a cell or from a cell line such as a hybridoma. The RNA is subjected to reverse transcription to produce cDNA. A nucleic acid that encodes an antibody heavy or light chain is amplified using one or more oligonucleotide primers or primer sets of the invention. The inventive primers can be used for amplification using other amplification techniques as well.

Oligonucleotides of the invention are listed in Table 1, which also indicates the portion of the antibody gene or cDNA to which the primer hybrizes, e.g., the constant region of a gamma chain (CG), the constant region of a lambda chain (CL), the constant region of a kappa chain (CK), the variable region of a heavy chain (VG), the variable region of a lambda chain (VL), or the variable region of a kappa chain (VK). It will be appreciated that certain primers hybridize to a coding or noncoding strand, therefore "hybridizes to" is intended to encompass either of these possibilities. Table 1 also indicates the number of individual sequences available from GenBank which can be grouped in a "family" which it should be possible to amplify using a particular primer. Certain of the primers, indicated as "short" do not contain engineered restriction sites. The other primers, which are longer, contain a restriction site for SfiI located 5' with respect to the portion that hybridizes to the antibody gene or cDNA. These primers also contain either CTC or CTCGC at the 5' end to improve efficiency of cleavage by the restriction enzyme. The invention encompasses additional oligonucleotides that comprise a portion having the sequence of a "short" primer of Table 1 and further comprise a restriction site located 5' with respect to the portion having the sequence of a short primer. The primers that comprise an SfiI site (indicated in bold) provide an example of how the short primers of the invention can be modified to incorporate a restriction site.

Thus in one aspect, the invention provides an oligonucleotide whose sequence comprises or consists of any of SEQ ID NOs: 1-44. In another aspect, the invention provides a primer mix containing at least two oligonucleotides selected from the group consisting of: SEQ ID NOs: 1-44. In another aspect, the invention provides a primer mix containing at least three oligonucleotides selected from the group consisting of: SEQ ID NOs: 1-44. In another aspect, the invention provides a primer mix containing at least four oligonucleotides selected from the group consisting of: SEQ ID NOs: 1-44. In another aspect, the invention provides a primer mix containing at least five oligonucleotides selected from the group consisting of: SEQ ID NOs: 1-44. In another aspect, the invention provides a primer mix containing at least six oligonucleotides selected from the group consisting of: SEQ ID NOs: 1-44. In certain embodiments of the invention at least one primer in a primer mix is a constant region primer and at least one primer in the primer mix is a variable region primer.

In some embodiments the primer mix contains at least one primer that hybridizes to a sequence that encodes at least a portion of the constant region of a gamma chain (a CG primer) and at least one primer that hybridizes to a sequence that encodes at least a portion of the variable region of a heavy chain (a VG primer). In some embodiments the primer mix contains at least one primer that hybridizes to a sequence that encodes at least a portion of the constant region of a lambda chain (a CL primer) and at least one primer that hybridizes a sequence that encodes at least a portion of the variable region of a lambda chain (a VL primer). In some embodiments the primer mix contains at least one primer that hybridizes to a sequence that encodes at least a portion of the constant region of a kappa chain (a CK) and at least one primer that hybridizes to a sequence that encodes at least a portion of the variable region of a kappa chain (a VK primer). In some embodiments of the invention the primer mix contains at least 2 or 3 VG primers and at least one CG primer. In some embodiments of the invention the primer mix contains at least 2 or 3 VL primers and at least one CL primer. In some embodiments of the invention the primer mix contains at least 2 or 3 VK primers and at least one CK primer. In any of the foregoing embodiments, the primers may be short or long. In some embodiments of the invention a first PCR reaction is performed using a primer set or pair of short primers and a second PCR reaction is performed suing a primer set or pair or primers that contain a restriction site (long primers). The long primers may comprise a sequence of a short primer as described in Example 1.

TABLE 1

RT-PCR primers

| Primer Name | | # Seq in Fam. | Degeneracy | DNA sequence |
|---|---|---|---|---|
| Constant Gamma | CG | 4 | none | 5'-CTCGCGGCCTCCGAGGCCTCATTTACCCKGAGACAGG-3' (SEQ ID NO: 1) |
| | CG-short | 4 | none | 5'-TCATTTACCCKGAGACAGG-3' (SEQ ID NO: 2) |
| Constant Lambda | CL | 4 | 2 | 5'-CTCGCGGCCTCCGAGGCCCTAAGAGCATTCTGRAGG-3' (SEQ ID NO: 3) |
| | CL-short | | | 5'-TAAGAGCATTCTGRAGG-3' (SEQ ID NO: 4) |
| Constant Kappa | CK | 1 | none | 5'-CTCGCGGCCTCCGAGGCCCTAACACTCTCCCCTGTTGA-3' (SEQ ID NO: 5) |
| | CL-short | | | 5'-TAACACTCTCCCCTGTTGA-3' (SEQ ID NO: 6) |
| Variable Heavy | VG1 + 7 | 8 | 4 | 5'-CTCGCGGCCCAGCCGGCCATGGACTGSAYCTGGAG-3' (SEQ ID NO: 7) |
| | VG2 | 3 | 4 | 5-'CTCGCGGCCCAGCCGGCCATGGACAYACTTTGCTMCAC-3' (SEQ ID NO: 8) |
| | VG3 | 21 | 24 | 5'-CTCGCGGCCCAGCCGGCCATGSAGTTKKGGCTGHGCTG-3' (SEQ ID NO: 9) |
| | VG4 | 7 | none | 5'-CTCGCGGCCCAGCCGGCCATGAAACACCTGTGGTTCTT-3' (SEQ ID NO: 10) |
| | VG5 | 1 | none | 5'-CTCGCGGCCCAGCCGGCCATGGGGTCAACCGCCATCCT-3' (SEQ ID NO: 11) |
| | VG6 | 1 | none | 5'-CTCGCGGCCCAGCCGGCCATGTCTGTCTCCTTCCTCAT-3' (SEQ ID NO: 12) |
| | VG1 + 7short | 8 | 4 | 5'-ATGGACTGSAYCTGGAG-3' (SEQ ID NO: 13) |
| | VG2 short | 3 | 4 | 5'-ATGGACAYACTTTGCTMCAC-3' (SEQ ID NO: 14) |
| | VG3 short | 21 | 24 | 5'-ATGSAGTTKKGGCTGHGCTG-3' (SEQ ID NO: 15) |
| | VG4 short | 7 | none | 5'-ATGAAACACCTGTGGTTCTT-3' (SEQ ID NO: 16) |
| | VG5 short | 1 | none | 5'-ATGGGGTCAACCGCCATCCT-3' (SEQ ID NO: 17) |
| | VG6 short | 1 | none | 5'-ATGTCTGTCTCCTTCCTCAT-3' (SEQ ID NO: 18) |
| Variable Lambda | VL1 | 5 | 24 | 5'-CTCGCGGCCCAGCCGGCCATGRCCDGSTYTCCTCTC-3' (SEQ ID NO: 19) |
| | VL2 | 5 | none | 5'-CTCGCGGCCCAGCCGGCCATGGCCTGGGCTCTGCTGCT-3' (SEQ ID NO: 20) |
| | VL3 | 8 | 24 | 5'-CTCGCGGCCCAGCCGGCCATGGCCTGGRYCVYTCTC-3' (SEQ ID NO: 21) |
| | VL4 | 1 | none | 5'-CTCGCGGCCCAGCCGGCCATGGCCTGGGGTCTCCTTCTA-3' (SEQ ID NO: 22) |
| | VL5 | 3 | 2 | 5'-CTCGCGGCCCAGCCGGCCATGGCCTGGACTCYTCTCCT-3' (SEQ ID NO: 23) |

TABLE 1-continued

RT-PCR primers

| | Primer Name | # Seq in Fam. | Degeneracy | DNA sequence |
|---|---|---|---|---|
| | VL6 + 9 | 2 | none | 5'-CTCGCGGCCCAGCCGGCCATGGCCTGGGCTCCACTACT-3' (SEQ ID NO: 24) |
| | VL7 | 2 | none | 5'-CTCGCGGCCCAGCCGGCCATGGCCTGGACTCCTCTCTT-3' (SEQ ID NO: 25) |
| | 10-54 + 8-61 | 2 | 8 | 5'-CTCGCGGCCCAGCCGGCCATGSCCTGGRTSATGCTTCT-3' (SEQ ID NO: 26) |
| | VL1-short | 5 | 24 | 5'-ATGRCCDGSTYTCCTCTC-3' (SEQ ID NO: 27) |
| | VL2-short | 5 | none | 5'-ATGGCCTGGGCTCTGCTGCT-3' (SEQ ID NO: 28) |
| | VL3-short | 8 | 24 | 5'-ATGGCCTGGRYCVYTCTC-3' (SEQ ID NO: 29) |
| | VL4-short | 1 | none | 5'-ATGGCCTGGGTCTCCTTCTA-3' (SEQ ID NO: 30) |
| | VL5-short | 3 | 2 | 5'-ATGGCCTGGACTCYTCTCCT-3' (SEQ ID NO: 31) |
| | VL6 + 9-short | 2 | none | 5'-ATGGCCTGGGCTCCACTACT-3' (SEQ ID NO: 32) |
| | VL7-short | 2 | none | 5'-ATGGCCTGGACTCCTCTCTT-3' (SEQ ID NO: 33) |
| | 10-54 + 8-61-short | 2 | 8 | 5'-ATGSCCTGGRTSATGCTTCT-3' (SEQ ID NO: 34) |
| Variable Kappa | VK1 | 16 | 2 | 5'-CTCGCGGCCCAGCCGGCCATGGACATGAGGGTCCYCGC-3' (SEQ ID NO: 35) |
| | VK2 + 1.8 | 10 | 4 | 5'-CTCGCGGCCCAGCCGGCCATGAGGSTCCYTGCTCAGCT-3' (SEQ ID NO: 36) |
| | VK3 | 6 | 2 | 5'-CTCGCGGCCCAGCCGGCCATGGAARCCCCAGCGCAGCT-3' (SEQ ID NO: 37) |
| | VK4 | 1 | none | 5'-CTCGCGGCCCAGCCGGCCATGGTGTTGCAGACCCAGGT-3' (SEQ ID NO: 38) |
| | VK5 | 1 | none | 5'-CTCGCGGCCCAGCCGGCCATGGGGTCCCAGGTTCACCT-3' (SEQ ID NO: 39) |
| | VK1-short | 16 | 2 | 5'-ATGGACATGAGGGTCCYCGC-3' (SEQ ID NO: 40) |
| | VK2 + 1.8-short | 10 | 4 | 5'-ATGAGGSTCCYTGCTCAGCT-3' (SEQ ID NO: 41) |
| | VK3-short | 6 | 2 | 5'-ATGGAARCCCCAGCGCAGCT-3' (SEQ ID NO: 42) |
| | VK4-short | 1 | none | 5'-ATGGTGTTGCAGACCCAGGT-3' (SEQ ID NO: 43) |
| | VK5-short | 1 | none | 5'-ATGGGGTCCCAGGTTCACCT-3' (SEQ ID NO: 44) |

It will be appreciated that the sequences listed in Table 1 represent either a single oligonucleotide molecule having the listed sequence or a population of oligonucleotide molecules each of which has the listed sequence. Certain of the primers listed in Table 1 are degenerate, i.e., the population of oligonucleotide molecules represented by the sequence contains individual members whose sequence differs at the degenerate position. The term "position" refers to a numerical value that is assigned to each nucleoside in a polynucleotide, generally with respect to the 5' end.

The concept of degenerate primers is well known in the art and is used herein consistently with the understanding in the art. Table 2 contains the IUPAC ambiguity code, which lists abbreviations that represent the nucleotides that may be present at a degenerate position. For example, K represents G or T.

TABLE 2

Ambiguity Code

| Abbreviation Letter | Nucleotide Represented |
|---|---|
| A | A |
| C | C |
| G | G |
| T | T |
| R | AG |
| Y | CT |
| M | AC |
| K | GT |
| W | AT |
| S | CG |
| B | CGT |
| D | AGT |
| H | ACT |
| V | ACG |
| N | ACGT |

If there are "N" possible nucleotides at a given position in an oligonucleotide, the position is said to be N-fold degenerate. Thus primer sequence "CG", i.e., 5'-CTCGCGGCCTC-CGAGGCCTCATTTACCCKGAGACAGG-3' (SEQ ID NO: 1) represents a population of oligonucleotides containing some members in which position 29 is occupied by a G and some members in which position 29 is occupied by a T. The invention includes oligonucleotides in which the degenerate position is occupied by any of the alternatives possible at that position. For example, the invention encompasses an oligonucleotide having the sequence of SEQ ID NO: 1, wherein position 29 is occupied by a G and also encompassess an oligonucleotide having the sequence of SEQ ID NO: 1, wherein position 29 is occupied by a T. All possibilities are encompassed. For example, primer "VG1+7 short" (SEQ ID NO: 13) is 2-fold degenerate at positions 9 and 11. Thus the invention encompasses 4 non-degenerate variants of SEQ ID NO: 13 in addition to encompassing the degenerate oligonucleotide represented by SEQ ID NO: 13, which contains oligonucleotide molecules having any of 4 different sequences. The invention also encompasses embodiments in which fewer of the positions are degenerate than indicated in Table 1. For example, the invention encompasses embodiments in which only position 9 of SEQ ID NO: 13 is degenerate (and position 11 is either of the nucleotides represented by Y) and embodiments in which only position 11 of SEQ ID NO: 13 is degenerate (and position 9 is either of the oligonucleotides represented by S).

The proportion of the different oligonucleotides in the oligonucleotide population of a degenerate oligonucleotide can vary. Typically each sequence is represented approximately equally in the population. However, it may be desirable to bias the composition of the mixture. Any specific percentage composition of a degenerate oligonucleotide listed in Table 1 is within the scope of the invention. The overall degeneracy of an oligonucleotide is the total number of different sequences that may be present in the oligonucleotide population. For example, if there are 3 degenerate positions, each of which is 2-fold degenerate, the degeneracy of the oligonucleotide population is $2^3=8$.

Expression Systems and Antibody Production

A nucleic acid encoding an antibody heavy or light chain isolated using any of the inventive oligonucleotide primers can be expressed in any of a wide variety of expression systems. An expression system is any suitable biological system such as a cell line or transgenic animal or plant capable of synthesizing a polypeptide. Typically the nucleic acid is inserted into an expression vector of which a wide variety are known. Suitable methods for expressing a polynucleotide of interest are known in the art and are described in Ausubel, supra, and in Sambrook, supra. See also, U.S. Pat. Nos. 4,816,567 and 6,331,415. Any prokaryotic or eukaryotic expression system can be used. In certain embodiments of the invention the expression system is not a hybridoma and is not a human being, i.e., the expression system is one that does not naturally produce the antibody chain.

In certain embodiments of the invention a plant-based expression system is used. A plant-based expression system is any expression system that employs cells of a plant or portion thereof. The expression system may be a plant cell line, whole plant, clonal root line, etc. The plant cell line, whole plant, clonal root line, etc., and may be transgenic or non-transgenic.

Methods and vectors for expressing a polynucleotide of interest, e.g, an antibody heavy or light chain in a plant-based expression system are well known in the art. See, e.g., U.S. Pat. No. 6,852,319. In certain embodiments of the invention a vector based on a plant viral genome is used. Without limitation, the invention encompasses the use of any vector based on a plant virus or viral genome, e.g., an RNA plant virus or viral genome, a DNA plant virus or viral genome, etc. See, e.g., U.S. Pat. Nos. 5,602,242, 5,500,360, and 5,846,795.

In certain embodiments of the invention transgenic or non-transgenic sprouts are used as an expression system. See, e.g., U.S. Pub. No. 20040093643 and U.S. Ser. No. 60/652,186, filed Feb. 11, 2005, entitled "Production of Foreign Nucleic Acids and Polypeptides in Sprout Systems" by Ensley, et al. In certain embodiments of the invention a clonal root line or other clonal line is used. See, e.g., U.S. Ser. No. 11/061,980, filed Feb. 18, 2005, entitled "SYSTEMS AND METHODS FOR CLONAL EXPRESSION IN PLANTS". Other patent applications containing relevant information for expressing a polynucleotide of interest include U.S. Pub. Nos. 20050026291, 20050114920, WO2005026375, WO0046350, WO0025574, WO2005049839, and U.S. Pat. No. 6,448,070.

The present invention expressly contemplates the expression of a nucleic acid that encodes a light chain or heavy chain of an antibody, wherein said nucleic acid is isolated using a method and/or primer disclosed herein using the expression systems and methods described in or referenced in any of the patent applications and publications listed in this section. Any specific plant, plant virus, plant viral replicon, etc., described therein can be used. In some embodiments the viral replicon contains sufficient sequence elements that it can be replicated in a plant cell, optionally utilizing components such as an RNA polymerase supplied by the plant in trans (e.g., the plant is transgenic or comprises another vector that expressed the RNA polymerase). The replicon may or may not include a coat protein gene or movement protein gene. Any particular method of introducing a plant virus or replicon into a plant or plant cell or plant part can be used. Examples include application to a plant part such as a leaf, abrasion (e.g., to introduce a viral transcript into a leaf), agroinfiltration, *Agrobacterium*-mediated transformation, biolistics, etc. The invention encompasses any plant viral vector or replicon that comprises a nucleic acid isolated according to a method described herein, e.g, a recombinant plant viral vector or replicon, and further encompasses a plant, plant part, or clonal culture derived from a plant, comprising the vector. The invention further encompasses a transgenic plant whose genome comprises the nucleic acid.

In some embodiments of the invention nucleic acid sequences that encode a heavy chain and a light chain are co-expressed so that the chains can associate with one another to form a complete antibody prior to harvest.

Any suitable method can be used to harvest and optionally purify an antibody chain or antibody produced according to the inventive methods.

Of course a heavy or light chain of an antibody can also be chemically synthesized. Having the nucleotide sequence that encodes the heavy or light chain provides the amino acid sequence.

A nucleic acid encoding an antibody heavy or light chain isolated using any of the inventive oligonucleotide primers can be modified in any of a variety of ways. For example, it may be modified so as to disrupt a glycosylation event or other post-translational processing event that would otherwise occur in eukaryotic cells. For example, a mutation that alters an amino acid that would be glycosylated or an adjacent or nearby site may be made. As is well known in the art, Asn-X-(Ser/Thr) is a sequence that can be recognized by eukaryotic N-linked glycosylation machinery. The particular site(s) to be modified may be selected taking into account the particular glycosylation machinery found in the expression system to be used. It may be modified to include a portion that encodes a polypeptide tag (e.g., to facilitate purification), a sequence that targets the antibody chain to a particular organelle, etc. A wide variety of alterations may be employed without interfering with the specific antigen binding properties of the antibody and are within the scope of the invention. In certain embodiments the alteration(s) result in an antibody that is at least 80% identical, at least 85% identical, at least 90% identical, at least 95% identical in sequence to the naturally occurring antibody.

An antibody produced according to the methods of the invention may be an antibody fragment such as an Fab', F(ab')$_2$, scFv (single-chain variable) or other fragment that retains an antigen binding site. The fragment may either be expressed as a fragment, i.e., a nucleic acid that encodes only the fragment may be expressed, or a complete antibody can be processed to produce a fragment using known techniques, e.g., cleavage or digestion.

Vectors

As mentioned above, a cDNA isolated using the inventive primers and methods can be inserted into a wide variety of vectors and expressed in a wide variety of cell types and expression systems. The invention provides additional vectors suitable for insertion of a nucleic acid isolated using the inventive primers that comprise a restriction site. The vector contains the same restriction site as present in the primers. The restriction site is present at one or more locations in the vector. In some embodiments a restriction site at an undesired location of the vector is removed, e.g., using site-directed mutagenesis. In some embodiments the restriction site is a restriction site for SfiI.

In a specific embodiment the invention provides a modified version of the binary vector pBI121, suitable for *Agrobacterium*-mediated transformation, in which the internal SfiI site at position 11031 is mutagenized and in which one or more new sites for SfiI is created. Briefly, pBI121 carries the neomycin phosphotransferase (NPTII) gene and α-glucuronidase (GUS) gene (Jefferson et al., *EMBO J*, 6: 3901-3907, 1987). The neomycin phosphotransferase (NPTII) gene is under the control of the nopaline synthase (nos) promoter and the terminator from nopaline synthase (nos) which provides polyadenylation signal. The neomycin phosphotransferase (NPTII) gene confers kanamycin resistance. The α-glucuronidase (GUS) activity is under the control of the cauliflower mosaic virus 35S promoter and the terminator from nopaline synthase (nos) provides polyadenylation. The invention provides a modified form of pBI121 in which the original SfiI site is mutagenized and in which two new SfiI sites are introduced to allow for convenient insertion of a heterologous nucleic acid such as a nucleic acid that encodes an antibody heavy or light chain.

Kits

The invention provides a kit comprising one or more oligonucleotides listed in Table 1. Preferably the kit contains at least two oligonucleotides. In specific embodiments the kit contains at least any number of oligonucleotides between 3 and 44. In general, the kit contains a pair or set of oligonucleotides suitable for amplifying a nucleic acid that encodes a heavy chain, e.g., a gamma heavy chain, and/or a pair or set of oligonucleotides suitable for amplifying a nucleic acid that encodes a light chain, e.g., a kappa or lambda light chain. In some embodiments the kit contains a pair or set of oligonucleotides suitable for amplifying a gamma heavy chain, a pair or set of oligonucleotides suitable for amplifying a kappa light chain, and a pair or set of oligonucleotides suitable for amplifying a lambda light chain. Any pair or set of oligonucleotides described above can be included in the kit. The kit will typically include instructions for using the kit to isolate nucleic acids that encode one or more chains of an antibody from a cell or cell line such as a hybridoma.

In addition to one or more oligonucleotides, the kit may further comprise any of a number of additional reagents. For example, the kit may contain reagents for performing a PCR reaction, e.g., an RT-PCR reaction. The kit may therefore contain, e.g., a reverse transcriptase, a thermostable DNA polymerase, nucleotides, buffers, etc. The kit may contain reagents for purifying RNA from a hybridoma or other cellular source of RNA.

The kit may contain one or more vectors into which a nucleic acid amplified using the kit can be inserted. The vector may be an expression vector that contains regulatory elements, e.g., a promoter, sufficient to direct expression in a cell, e.g., a plant cell, bacterial cell, fungal cell, insect cell, mammalian cell, etc. Other appropriate elements such as transcriptional terminators, etc., can also be included. A wide variety of expression vectors are available in the art, and any of these can be included in the kit. In one embodiment the vector is a binary vector suitable for *Agrobacterium*-mediated transformation.

The vector may contain one or more convenient restriction sites such that cleavage of the vector with a restriction enzyme results in a "sticky end" that is compatible with, i.e., hybridizes to, a restriction site present in one or more of the oligonucleotide primers present in the kit. In some embodiments the vector contains one or more restriction sites for an enzyme that recognizes an 8 nucleotide recognition site. The 8 nucleotides may be continuous or may be separated by one or more other nucleotides (e.g., 1-10 nucleotides) that are not specifically recognized, though the spacing may be essential for recognition. For example, in certain embodiments the enzyme cuts within XXXXNNNNNXXXX, where N stands for any nucleotide and X stands for any specific nucleotide (i.e., each X is independently selected). Such sites can be advantageous as they allow one to perform directional cloning using only one enzyme by having a different sequence of 5 nucleotides at the 5'- and 3'-ends of the insert. In some embodiments the vector contains one or more restriction sites for SfiI, which cuts within the site GGCCNNNNNGGCC. The vector can be provided in linearized or circular form. A restriction enzyme for cleaving the vector may also be provided. Reagents for performing a ligation, e.g., ligase, ligase buffer, etc., can be included.

An identifier, e.g., a bar code, radio frequency ID tag, etc., may be present in or on the kit. The identifier can be used, e.g., to uniquely identify the kit for purposes of quality control, inventory control, tracking, movement between workstations, etc.

Kits will generally include one or more vessels or containers so that certain of the individual reagents may be separately housed. The kits may also include a means for enclosing the individual containers in relatively close confinement for commercial sale, e.g., a plastic box, in which instructions, packaging materials such as styrofoam, etc., may be enclosed.

Nucleotide Sequences Encoding Human Monoclonal Antibodies to Anthrax Antigens and Isolated Heavy and Light Chains As described in more detail in Example 1, the primers listed in Table 1 were used to isolate cDNA sequences encoding the gamma heavy chain and the kappa light chain of two different human monoclonal antibodies (huMAbs). Isolation of these cDNAs is exemplary of the use of the oligonucleotide primers of the invention. One of the huMAbs specifically binds to domain 4 of the *Bacillus anthracis* protective antigen (PA) polypeptide, designated PA-1. The other huMAb specifically binds to the *Bacillus anthracis* lethal factor (LF) polypeptide, designated LF-1. *Bacillus anthracis* is the causative agent of anthrax. The roles of PA and LF in bacterial pathogenesis and in the immune response are well known in the art. cDNA sequences were isolated from hybridoma cell lines that were obtained by fusing lymphocytes from an individual who had received an anthrax vaccination with myeloma cells and screening for antibodies specific for *B. anthracis* using standard methods.

Provided are isolated nucleic acids comprising a DNA sequence of the PA-1 huMAb Kappa light chain cDNA (SEQ ID NO: 45), a DNA sequence of PA-1 huMAb Gamma heavy chain cDNA (SEQ ID NO: 47), a DNA sequence of LF-1 huMAb Kappa light chain cDNA (SEQ ID NO: 49), or a DNA sequence of LF-1 huMAb Gamma heavy chain cDNA (SEQ ID NO: 51). The invention also provides corresponding RNA sequences, in which T is replaced by U.

The invention also provides an isolated polypeptide encoded by any one of SEQ ID NOs 45, 47, 49, or 51. The amino acid sequences of these polypeptides are set forth in SEQ ID NOs 46, 48, 50, and 52. The invention also provides an isolated polypeptide that is at least 80%, at least 85%, at least 90%, at least 95%, or more identical to a polypeptide of SEQ ID NOs 46, 48, 50, or 52. The invention also provides antibody compositions in which one or more of SEQ ID NOs 45, 47, 49, or 51 is expressed in an expression system other than a hybridoma or human being.

DNA sequence of PA-1 huMAb Kappa light chain cDNA:
(SEQ ID NO: 45)
5'-ATGGAAGCCCCAGCGCAGCTTCTCTTCCTCCTGCTACTCTGGCTCCC

AGATACCACCGGAGAAATTGTGTTGACGCAGTCTCCAGGCACCCTGTCTT

TGTCTCCAGGGGAAAGAGCCACCCTCTCCTGCAGGGCCAGTCAGAGTGTT

AGCTACAGCTCCTTAGCCTGGTACCAGCAGAAACCTGGCCAGGCTCCCAG

CCTCCTCATCTATGGTGCATCCAGCAGGGCCACTGGCATCCCAGACAGGT

TCAGTGGCAGTGGGTCTGGGCCAGACTTCACTCTCACCATCAGCAGACTG

GAGCCTGAAGATTTTGCAGTTTATTACTGTCAGCACTATGGTAACTCACC

GTACACTTTTGGCCAGGGGACCAAGCTGGAGATCAAACGAACTGTGGCTG

CACCATCTGTCTTCATCTTCCCGCCATCTGATGAGCAGTTGAAATCTGGA

ACTGCCTCTGTTGTGTGCCTGCTGAATAACTTCTATCCCAGAGAGGCCAA

AGTACAGTGGAAGGTGGATAACGCCCTCCAATCGGGTAACTCCCAGGAGA

GTGTCACAGAGCAGGACAGCAAGGACAGCACCTACAGCCTCAGCAGCACC

CTGACGCTGAGCAAAGCAGACTACGAGAAACACAAAGTCTACGCCTGCGA

AGTCACCCATCAGGGCCTGAGCTCGCCCGTCACAAAGAGCTTCAACAGGG

GAGAGTGTTAG-3'

Amino acid sequence of PA-1 huMAb Kappa light chain:
(SEQ ID NO: 46)
MEAPAQLLFLLLLWLPDTTGEIVLTQSPGTLSLSPGERATLSCRASQSVS

YSSLAWYQQKPGQAPSLLIYGASSRATGIPDRFSGSGSGPDFTLTISRLE

PEDFAVYYCQHYGNSPYTFGQGTKLEIKRTVAAPSVFIFPPSDEQLKSGT

ASVVCLLNNFYPREAKVQWKVDNALQSGNSQESVTEQDSKDSTYSLSSTL

TLSKADYEKHKVYACEVTHQGLSSPVTKSFNRGEC

The CDR sequences of PA-1 huMAb Kappa light chain are depicted in bold, and correspond to amino acid residues 50-61 (PA-1CDR1), amino acid residues 77-83 (PA-1CDR2), and amino acid residues 116-124 (PA-1CDR3) of SEQ ID NO:46. Isolated, each of the CDR sequences consist of:

```
PA-1CDR1:  RASQSVSYSSLA      (SEQ ID NO: 59)
PA-1CDR2:  GASSRAT           (SEQ ID NO: 60)
PA-1CDR3:  QHYGNSPYT         (SEQ ID NO: 61)
```

DNA sequence of PA-1 huMAb Gamma heavy chain cDNA:
(SEQ ID NO: 47)
5'-ATGGACTGGATCTGGAGGATCCTCTTTTTGGTGGCAGCAGCCACAGG

TGCCCACTCCCAGGTCCAGCTTGTGCAGTCTGGGGCTGAGGTGAAGAAGC

CTGGGGCCTCAGTGAAGGTTTCCTGCAAGGCCTCTGGATACACCTTCACT

AGCAATGCTATACAATGGGTGCGCCAGGCCCCCGGACAAAGGCTTGAGTG

GGTGGGATGGATCAACGGTGGCGATGGTAACACAAAATATTCACAGAAGT

TCCAGGGCAGAGTCACCATTAGTAGGGACATATCCGCGAGCACAGCCTAC

ATGGAGCTGAGCAGCCTGAGATCTGAAGACACGGCTGTGTATTACTGTGC

GAGACATCGTTTGCAAAGAGGGGGGTTCGACCCCTGGGGCCAGGGAACCC

TGGTCACCGTCTCCTCAGCCTCCACCAAGGGCCCATCGGTCTTCCCCCTG

GCACCTTCCTCCAAGAGCACCTCTGGGGGCACAGCGGCCCTGGGCTGCCT

GGTCAAGGACTACTTCCCCGAACCGGTGACGGTGTCGTGGAACTCAGGCG

CCCTGACCAGCGGCGTGCACACCTTCCCGGCTGTCCTACAGTCCTCAGGA

CTCTACTCCCTCAGCAGCGTGGTGACCGTGCCCTCCAGCAGCTTGGGCAC

CCAGACCTACATCTGCAACGTGAATCACAAGCCCAGCAACACCAAGGTGG

ACAAGAGAGTTGAGCCCAAATCTTGTGACAAAACTCACACATGCCCACCG

TGCCCAGCACCTGAACTCCTGGGGGGACCGTCAGTCTTCCTCTTCCCCCC

AAAACCCAAGGACACCCTCATGATCTCCCGGACCCCTGAGGTCACATGCG

TGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCA

GTACAACAGCACGTACCGTGTGGTCAGCGTCCTCACCGTCCTGCACCAGG

ACTGGCTGAATGGCAAGGAGTACAAGTGCAAGGTCTCCAACAAAGCCCTC

CCAGCCCCCATCGAGAAAACCATCTCCAAAGCCAAAGGGCAGCCCCGAGA

ACCACAGGTGTACACCCTGCCCCCATCCCGGGAGGAGATGACCAAGAACC

AGGTCAGCCTGACCTGCCTGGTCAAAGGCTTCTATCCCAGCGACATCGCC

GTGGAGTGGGAGAGCAATGGGCAGCCGGAGAACAACTACAAGACCACGCC

TCCCGTGCTGGACTCCGACGGCTCCTTCTTCCTCTATAGCAAGCTCACCG

TGGACAAGAGCAGGTGGCAGCAGGGGAACGTCTTCTCATGCTCCGTGATG

CATGAGGCTCTGCACAACCACTACACGCAGAAGAGCCTCTCCCTGTCTCC

GGGTAAATGA-3'

Amino acid sequence of PA-1 huMAb Gamma heavy chain:
(SEQ ID NO: 48)
MDWIWRILFLVAAATGAHSQVQLVQSGAEVKKPGASVKVSCKASGYTFTS

NAIQWVRQAPGQRLEWVGWINGGDGNTKYSQKFQGRVTISRDISASTAYM

ELSSLRSEDTAVYYCARHRLQRGGFDPWGQGTLVTVSSASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKRVEPKSCDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPGK

The CDR sequences of PA-1 huMAb Gamma heavy chain are depicted in bold, and correspond to amino acid residues 51-60 (PA-hCDR1), amino acid residues 75-90 (PA-hCDR2), and amino acid residues 124-133 (PA-hCDR3) of SEQ ID NO:48.

```
PA-hCDR1:  GYTFTSNAIQ        (SEQ ID NO: 62)
PA-hCDR2:  WINGGDGNTKYSQKFQG (SEQ ID NO: 63)
PA-hCDR3:  HRLQRGGFDP        (SEQ ID NO: 64)
```

In certain embodiments, an isolated antibody or functional fragment thereof is provided, wherein the antibody comprises one or more light chain (LC) complementary determining regions (CDRs) selected from (i) a light chain CDR1 with at least 90% sequence identity to PA-1CDR1: RASQSVSYSSLA (SEQ ID NO:59); (ii) a light chain CDR2 with at least 90% sequence identity to PA-1CDR2: GASSRAT (SEQ ID NO:60); and (iii) a light chain CDR3 with at least 90% sequence identity to PA-1CDR3: QHYGNSPYT (SEQ ID NO:61), and the antibody or functional fragment thereof can bind specifically to B. anthracis protective antigen. In some embodiments, an isolated antibody or functional fragment thereof is provided, wherein the antibody comprises two or more light chain (LC) complementary determining regions (CDRs) selected from (i) a light chain CDR1 with at least 90% sequence identity to PA-1CDR1: RASQSVSYSSLA (SEQ ID NO:59); (ii) a light chain CDR2 with at least 90% sequence identity to PA-1CDR2: GASSRAT (SEQ ID NO:60); and (iii) a light chain CDR3 with at least 90% sequence identity to PA-(CDR3: QHYGNSPYT (SEQ ID NO:61), and the antibody or functional fragment thereof can bind specifically to B. anthracis protective antigen. In some embodiments, an isolated antibody or functional fragment thereof is provided, wherein the antibody comprises three light chain (LC) complementary determining regions (CDRs) consisting of (i) a light chain CDR1 with at least 90% sequence identity to PA-1CDR1: RASQSVSYSSLA (SEQ ID NO:59); (ii) a light chain CDR2 with at least 90% sequence identity to PA-1CDR2: GASSRAT (SEQ ID NO:60); and (iii) a light chain CDR3 with at least 90% sequence identity to PA-1CDR3: QHYGNSPYT (SEQ ID NO:61), and the antibody or functional fragment thereof can bind specifically to B. anthracis protective antigen. Nucleic acid compositions encoding the foregoing antibody or fragment sequences are further provided.

In certain embodiments, an isolated antibody or functional fragment thereof is provided, wherein the antibody comprises one or more heavy chain (HC) complementary determining regions (CDRs) selected from (i) a heavy chain CDR1 with at least 90% sequence identity to PA-hCDR1: GYTFTSNAIQ (SEQ ID NO:62); (ii) a heavy chain CDR2 with at least 90% sequence identity to PA-hCDR2: WINGGDGNTKYSQKFQG (SEQ ID NO:63); and (iii) a heavy chain CDR3 with at least 90% sequence identity to PA-hCDR3: HRLQRGGFDP (SEQ ID NO:64), and the antibody or functional fragment thereof can bind specifically to B. anthracis protective antigen. In some embodiments, an isolated antibody or functional fragment thereof is provided, wherein the antibody comprises two or more heavy chain (HC) complementary determining regions (CDRs) selected from (i) a heavy chain CDR1 with at least 90% sequence identity to PA-hCDR1: GYTFTSNAIQ (SEQ ID NO:62); (ii) a heavy chain CDR2 with at least 90% sequence identity to PA-hCDR2: WINGGDGNTKYSQKFQG (SEQ ID NO:63); and (iii) a heavy chain CDR3 with at least 90% sequence identity to PA-hCDR3: HRLQRGGFDP (SEQ ID NO:64), and the antibody or functional fragment thereof can bind specifically to B. anthracis protective antigen. In some embodiments, an isolated antibody or functional fragment thereof is provided, wherein the antibody comprises three heavy chain (HC) complementary determining regions (CDRs) consisting of (i) a heavy chain CDR1 with at least 90% sequence identity to PA-hCDR1: GYTFTSNAIQ (SEQ ID NO:62); (ii) a heavy chain CDR2 with at least 90% sequence identity to PA-hCDR2: WINGGDGNTKYSQKFQG (SEQ ID NO:63); and (iii) a heavy chain CDR3 with at least 90% sequence identity to PA-hCDR3: HRLQRGGFDP (SEQ ID NO:64), and the antibody or functional fragment thereof can bind specifically to B. anthracis protective antigen. Nucleic acid compositions encoding the foregoing antibody or fragment sequences are further provided.

In some embodiments, an isolated antibody or functional fragment is provided wherein the antibody comprises three light chain (LC) complementary determining regions (CDRs) consisting of: (i) a light chain CDR1 with at least 90% sequence identity to PA-1CDR1: RASQSVSYSSLA (SEQ ID NO:59), (ii) a light chain CDR2 with at least 90% sequence identity to PA-1CDR2: GASSRAT (SEQ ID NO:60), and (iii) a light chain CDR3 with at least 90% sequence identity to PA-1CDR3: QHYGNSPYT (SEQ ID NO:61); and three heavy chain complementary determining regions (CDRs) consisting of (i) a heavy chain CDR1 with at least 90% sequence identity to PA-hCDR1: GYTFTSNAIQ (SEQ ID NO:62), (ii) a heavy chain CDR2 with at least 90% sequence identity to PA-hCDR2: WINGGDGNTKYSQKFQG (SEQ ID NO:63); and (iii) a heavy chain CDR3 with at least 90% sequence identity to PA-hCDR3: HRLQRGGFDP (SEQ ID NO:64); and the antibody or functional fragment thereof can bind specifically to B. anthracis protective antigen.

In certain embodiments, an isolated antibody or functional fragment thereof is provided, wherein the antibody comprises one or more light chain (LC) complementary determining regions (CDRs) selected from (i) a light chain PA-1CDR1: RASQSVSYSSLA (SEQ ID NO:59); (ii) a light chain PA-1CDR2: GASSRAT (SEQ ID NO:60); and (iii) a light chain PA-1CDR3: QHYGNSPYT (SEQ ID NO:61), and the antibody or functional fragment thereof can bind specifically to B. anthracis protective antigen. In some embodiments, an isolated antibody or functional fragment thereof is provided, wherein the antibody comprises two or more light chain (LC) complementary determining regions (CDRs) selected from (i) a light chain PA-1CDR1: RASQSVSYSSLA (SEQ ID NO:59); (ii) a light chain PA-1CDR2: GASSRAT (SEQ ID NO:60); and (iii) a light chain PA-1CDR3: QHYGNSPYT (SEQ ID NO:61), and the antibody or functional fragment thereof can bind specifically to B. anthracis protective antigen. In some embodiments, an isolated antibody or functional fragment thereof is provided, wherein the antibody comprises three light chain (LC) complementary determining regions (CDRs) consisting of (i) a light chain PA-1CDR1: RASQSVSYSSLA (SEQ ID NO:59); (ii) a light chain PA-1CDR2: GASSRAT (SEQ ID NO:60); and (iii) a light chain PA-1CDR3: QHYGNSPYT (SEQ ID NO:61), and the antibody or functional fragment thereof can bind specifically to B. anthracis protective antigen. Nucleic acid compositions encoding the foregoing antibody or fragment sequences are further provided.

In certain embodiments, an isolated antibody or functional fragment thereof is provided, wherein the antibody comprises one or more heavy chain (HC) complementary determining regions (CDRs) selected from (i) a heavy chain PA-hCDR1: GYTFTSNAIQ (SEQ ID NO:62); (ii) a heavy chain PA-hCDR2: WINGGDGNTKYSQKFQG (SEQ ID NO:63); and (iii) a heavy chain PA-hCDR3: HRLQRGGFDP (SEQ ID NO:64), and the antibody or functional fragment thereof can bind specifically to B. anthracis protective antigen. In some embodiments, an isolated antibody or functional fragment thereof is provided, wherein the antibody comprises two or more heavy chain (HC) complementary determining regions (CDRs) selected from (i) a heavy chain PA-hCDR1: GYTFTSNAIQ (SEQ ID NO:62); (ii) a heavy chain PA-hCDR2: WINGGDGNTKYSQKFQG (SEQ ID NO:63); and (iii) a heavy chain PA-hCDR3: HRLQRGGFDP (SEQ ID NO:64), and the antibody or functional fragment thereof can bind specifically to B. anthracis protective antigen. In some embodiments, an isolated antibody or functional fragment thereof is provided, wherein the antibody comprises three heavy chain (HC) complementary determining regions (CDRs) consisting of (i) a heavy chain PA-hCDR1: GYTFT-SNAIQ (SEQ ID NO:62); (ii) a heavy chain PA-hCDR2: WINGGDGNTKYSQKFQG (SEQ ID NO:63); and (iii) a heavy chain PA-hCDR3: HRLQRGGFDP (SEQ ID NO:64), and the antibody or functional fragment thereof can bind specifically to B. anthracis protective antigen. Nucleic acid compositions encoding the foregoing antibody or fragment sequences are further provided.

In some embodiments, an isolated antibody or functional fragment is provided wherein the antibody comprises three light chain (LC) complementary determining regions (CDRs) consisting of: (i) a light chain PA-1CDR1: RASQSV-SYSSLA (SEQ ID NO:59), (ii) a light chain PA-1CDR2: GASSRAT (SEQ ID NO:60), and (iii) a light chain PA-1CDR3: QHYGNSPYT (SEQ ID NO:61); and three heavy chain complementary determining regions (CDRs) consisting of (i) a heavy chain PA-hCDR1: GYTFTSNAIQ (SEQ ID NO:62), (ii) a heavy chain PA-hCDR2: WING-GDGNTKYSQKFQG (SEQ ID NO:63); and (iii) a heavy chain PA-hCDR3: HRLQRGGFDP (SEQ ID NO:64); and the antibody or functional fragment thereof can bind specifically to B. anthracis protective antigen.

In certain embodiments, a PA-1 antibody functional fragment is any one of an Fv, Fab, F(ab)$_2$ or an scFV functional fragment.

```
DNA sequence of LF-1 huMAb Kappa light chain cDNA:
                                        (SEQ ID NO: 49)
ATGTTGCCATCACAACTCATTGGGTTTCTGCTGCTCTGGGTTCCAGCCTC

CAGGGGTGAAATTGTGCTGACTCAGTCTCCAGACTTTCAGTCTGTGAGTC

CAAAGGAGAAAGTCACCATCACCTGCCGGGCCAGCCAGAGCGTTGGTAGT

AGCTTACACTGGTACCAGCAGAAACCAGATCAGTCTCCAAAGCTCCTCAT

CAAGTATGCTTCCCAGTCCTTCTCAGGGGTCCCCTCGAGGTTCAGTGGCA

GTGGATCTGGGACAGATTTCACCCTCACCATCAATAGCCTGGAAACTGAA

GATGCTGCAACGTATTACTGTCATCAGAGTAGTAGTTTACCTCTCACTTT

CGGCGGAGGGACCAAGGTGGAGATCAAACGAACTGTGGCTGCACCATCTG

TCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAG

AGCAGGACAGCAAGGACAGCACCTACAGCCTCAGCAGCACCCTGACGCTG

AGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGTT

AG

Amino acid sequence of LF-1 huMAb Kappa light
chain:
                                        (SEQ ID NO: 50)
MLPSQLIGFLLLWVPASRGEIVLTQSPDFQSVSPKEKVTITCRASQSVGS

SLHWYQQKPDQSPKLLIYASQSFSGVPSRFSGSGSGTDFTLTINSLETE

DAATYYCHQSSSLPLTFGGGTKVEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC
```

The CDR sequences of LF-1 huMAb Kappa light chain are depicted in bold, and correspond to amino acid residues 51-60 (LF-1CDR1), amino acid residues 75-90 (LF-1CDR2), and amino acid residues 124-133 (LF-1CDR3) of SEQ ID NO:50.

```
LF-1CDR1: RASQSVGSSLH        (SEQ ID NO: 65)

LF-1CDR2: YASQSFS            (SEQ ID NO: 66)

LF-1CDR3: HQSSSLPLT          (SEQ ID NO: 67)

DNA sequence of LF-1 huMAb Gamma heavy chain cDNA:
                                        (SEQ ID NO: 51)
ATGGAGTTGGGGCTGTGCTGGCTTTTTCTTGTGGCTATTTTAAAAGGTGT

CCAGTGTGAGGTGCAGCTGTTGGAGTCTGGGGGAGGCTTGGTACAGCCGG

GGGGGTCCCTGAGACTCTCCTGTTCTGGCTCTGGATTCATGTTTAGCAGT

TATGCCATGAGCTGGGTCCGCCAGGCTCCAGGGAAGGGGCTGGAGTGGGT

CTCAGGAATTAGTGGTAGCGGTGGTACTACAAACTACGCAGACTCCGTGA

AGGGCCGGTTCACCATCTCCAGAGACAATTCCAAGAACACGCTGTATATG

CAAATGAACAGCCTGAGAGCCGAGGACACGGCCGTATATTACTGTGCGAA

AGATGGGTATATGGCCGACTGGGGGGTTCTGACTACTGGGGCCAGGGAA

CCCTGGTCACCGTCTCCTCAGCCTCCACCAAGGGCCCATCAGTCTTCCCC

CTGGCACCCTCCTCCAAGAGCACCTCTGGGGGCACAGCGGCCCTGGGCTG

CCTGGTCAAGGACTACTTCCCCGAACCGGTGACGGTGTCGTGGAACTCAG

GCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGG

CACCCAGACCTACATCTGCAACGTGAATCACAAGCCCAGCAACACCAAGG

TGGACAAGAAAGTTGAGCCCAAATCTTGTGACAAAACTCACACATGCCCA

CCGTGCCCAGCACCTGAACTCCTGGGGGGACCGTCAGTCTTCCTCTTCCC

CCCAAAACCCAAGGACACCCTCATGATCTCCCGGACCCCTGAGGTCACAT

GCGTGGTGGTGGACGTGAGCCACGAAGACCCTGAGGTCAAGTTCAACTGG

TACGTGGACGGCGTGGAGGTGCATAATGCCAAGACAAAGCCGCGGGAGGA

GCAGTACAACAGCACGTACCGTGTGGTCAGCGTCCTCACCGTCCTGCACC

AGGACTGGCTGAATGGCAAGGAGTACAAGTGCAAGGTCTCCAACAAAGCC

CTCCCAGCCCCCATCGAGAAAACCATCTCCAAAGCCAAAGGGCAGCCCCG

AGAACCACAGGTGTACACCCTGCCCCCATCCCGGGATGAGCTGACCAAGA

ACCAGGTCAGCCTGACCTGCCTGGTCAAAGGCTTCTATCCCAGCGACATC

GCCGTGGAGTGGGAGAGCAATGGGCAGCCGGAGAACAACTACAAGACCAC

GCCTCCCGTGCTGGACTCCGACGGCTCCTTCTTCCTCTACAGCAAGCTCA

CCGTGGACAAGAGCAGGTGGCAGCAGGGGAACGTCTTCTCATGCTCCGTG

ATGCATGAGGGTCTGCACAACCACTACACGCAGAAGAGCCTCTCCCTGTC

TCCGGGTAAATGA

Amino acid sequence of LF-1 huMAb Gamma heavy
chain:
                                        (SEQ ID NO: 52)
MELGLCWLFLVAILKGVQCEVQLLESGGGLVQPGGSLRLSCSGSGFMFSS

YAMSWVRQAPGKGLEWVSGISGSGGTTNYADSVKGRFTISRDNSKNTLYM

QMNSLRAEDTAVYYCAKDGVYGRLGGSDYWGQGTLVTVSSASTKGPSVFP
```

```
LAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCSV

MHEGLHNHYTQKSLSLSPGK
```

The CDR sequences of LF-1 huMAb Gamma heavy chain are depicted in bold, and correspond to amino acid residues 51-60 (LF-hCDR1), amino acid residues 75-90 (LF-hCDR2), and amino acid residues 124-133 (LF-hCDR3) of SEQ ID NO:52.

```
LF-hCDR1: GFMFSSYAMS         (SEQ ID NO: 68)

LF-hCDR2: GISGSGGTTNYADSVKG  (SEQ ID NO: 69)

LF-hCDR3: DGVYGRLGGSDY       (SEQ ID NO: 70)
```

In certain embodiments, an isolated antibody or functional fragment thereof is provided, wherein the antibody comprises one or more light chain (LC) complementary determining regions (CDRs) selected from (i) a light chain CDR1 with at least 90% sequence identity to LF-1CDR1: RASQSVGSSLH (SEQ ID NO:65), (ii) a light chain CDR2 with at least 90% sequence identity to LF-1CDR2: YASQSFS (SEQ ID NO:66); and (iii) a light chain CDR3 with at least 90% sequence identity to LF-1CDR3: HQSSSLPLT (SEQ ID NO:67), and the antibody or functional fragment thereof can bind specifically to B. anthracis lethal factor. In some embodiments, an isolated antibody or functional fragment thereof is provided, wherein the antibody comprises two or more light chain (LC) complementary determining regions (CDRs) selected from (i) a light chain CDR1 with at least 90% sequence identity to LF-1CDR1: RASQSVGSSLH (SEQ ID NO:65), (ii) a light chain CDR2 with at least 90% sequence identity to LF-1CDR2: YASQSFS (SEQ ID NO:66), and (iii) a light chain CDR3 with at least 90% sequence identity to LF-1CDR3: HQSSSLPLT (SEQ ID NO:67), and the antibody or functional fragment thereof can bind specifically to B. anthracis lethal factor. In some embodiments, an isolated antibody or functional fragment thereof is provided, wherein the antibody comprises three light chain (LC) complementary determining regions (CDRs) consisting of (i) a light chain CDR1 with at least 90% sequence identity to LF-1CDR1: RASQSVGSSLH (SEQ ID NO:65), (ii) a light chain CDR2 with at least 90% sequence identity to LF-1CDR2: YASQSFS (SEQ ID NO:66), and (iii) a light chain CDR3 with at least 90% sequence identity to LF-1CDR3: HQSSSLPLT (SEQ ID NO:67), and the antibody or functional fragment thereof can bind specifically to B. anthracis lethal factor. Nucleic acid compositions encoding the foregoing antibody or fragment sequences are further provided.

In certain embodiments, an isolated antibody or functional fragment thereof is provided, wherein the antibody comprises one or more heavy chain (HC) complementary determining regions (CDRs) selected from (i) a heavy chain CDR1 with at least 90% sequence identity to LF-hCDR1: GFMFSSYAMS (SEQ ID NO:68); (ii) a heavy chain CDR2 with at least 90% sequence identity to LF-hCDR2: GISGSGGTTNYADSVKG (SEQ ID NO:69); and (iii) a heavy chain CDR3 with at least 90% sequence identity to LF-hCDR3: DGVYGRLGGSDY (SEQ ID NO:70), and the antibody or functional fragment thereof can bind specifically to B. anthracis lethal factor. In some embodiments, an isolated antibody or functional fragment thereof is provided, wherein the antibody comprises two or more heavy chain (HC) complementary determining regions (CDRs) selected from (i) a heavy chain CDR1 with at least 90% sequence identity to LF-hCDR1: GFMFSSYAMS (SEQ ID NO:68); (ii) a heavy chain CDR2 with at least 90% sequence identity to LF-hCDR2: GISGSGGTTNYADSVKG (SEQ ID NO:69); and (iii) a heavy chain CDR3 with at least 90% sequence identity to LF-hCDR3: DGVYGRLGGSDY (SEQ ID NO:70), and the antibody or functional fragment thereof can bind specifically to B. anthracis lethal factor. In some embodiments, an isolated antibody or functional fragment thereof is provided, wherein the antibody comprises three heavy chain (HC) complementary determining regions (CDRs) consisting of (i) a heavy chain CDR1 with at least 90% sequence identity to LF-hCDR1: GFMFSSYAMS (SEQ ID NO:68); (ii) a heavy chain CDR2 with at least 90% sequence identity to LF-hCDR2: GISGSGGTTNYADSVKG (SEQ ID NO:69); and (iii) a heavy chain CDR3 with at least 90% sequence identity to LF-hCDR3: DGVYGRLGGSDY (SEQ ID NO:70), and the antibody or functional fragment thereof can bind specifically to B. anthracis lethal factor. Nucleic acid compositions encoding the foregoing antibody or fragment sequences are further provided.

In some embodiments, an isolated antibody or functional fragment is provided wherein the antibody comprises three light chain (LC) complementary determining regions (CDRs) consisting of: (i) a light chain CDR1 with at least 90% sequence identity to LF-1CDR1: RASQSVGSSLH (SEQ ID NO:65), (ii) a light chain CDR2 with at least 90% sequence identity to LF-1CDR2: YASQSFS (SEQ ID NO:66); and (iii) a light chain CDR3 with at least 90% sequence identity to LF-(CDR3: HQSSSLPLT (SEQ ID NO:67), and three heavy chain complementary determining regions (CDRs) consisting of (i) a heavy chain CDR1 with at least 90% sequence identity to LF-hCDR1: GFMFSSYAMS (SEQ ID NO:68); (ii) a heavy chain CDR2 with at least 90% sequence identity to LF-hCDR2: GISGSGGTTNYADSVKG (SEQ ID NO:69); and (iii) a heavy chain CDR3 with at least 90% sequence identity to LF-hCDR3: DGVYGRLGGSDY (SEQ ID NO:70), and the antibody or functional fragment thereof can bind specifically to B. anthracis lethal factor.

In certain embodiments, an isolated antibody or functional fragment thereof is provided, wherein the antibody comprises one or more light chain (LC) complementary determining regions (CDRs) selected from (i) a light chain LF-1CDR1: RASQSVGSSLH (SEQ ID NO:65), (ii) a light chain LF-1CDR2: YASQSFS (SEQ ID NO:66); and (iii) a light chain LF-1CDR3: HQSSSLPLT (SEQ ID NO:67), and the antibody or functional fragment thereof can bind specifically to B. anthracis lethal factor. In some embodiments, an isolated antibody or functional fragment thereof is provided, wherein the antibody comprises two or more light chain (LC) complementary determining regions (CDRs) selected from (i) a light chain LF-1CDR1: RASQSVGSSLH (SEQ ID NO:65), (ii) a light chain LF-1CDR2: YASQSFS (SEQ ID NO:66), and (iii) a light chain LF-1CDR3: HQSSSLPLT (SEQ ID NO:67), and the antibody or functional fragment thereof can bind specifically to B. anthracis lethal factor. In some embodiments, an isolated antibody or functional fragment thereof is provided, wherein the antibody comprises three light chain (LC) complementary determining regions (CDRs) consisting of (i) a light chain LF-1CDR1: RASQSVGSSLH (SEQ ID NO:65), (ii) a light chain LF-1CDR2:

YASQSFS (SEQ ID NO:66), and (iii) a light chain LF-1CDR3: HQSSSLPLT (SEQ ID NO:67), and the antibody or functional fragment thereof can bind specifically to *B. anthracis* lethal factor. Nucleic acid compositions encoding the foregoing antibody or fragment sequences are further provided.

In certain embodiments, an isolated antibody or functional fragment thereof is provided, wherein the antibody comprises one or more heavy chain (HC) complementary determining regions (CDRs) selected from (i) a heavy chain LF-hCDR1: GFMFSSYAMS (SEQ ID NO:68); (ii) a heavy chain LF-hCDR2: GISGSGGTTNYADSVKG (SEQ ID NO:69); and (iii) a heavy chain LF-hCDR3: DGVYGRLGGSDY (SEQ ID NO:70), and the antibody or functional fragment thereof can bind specifically to *B. anthracis* lethal factor. In some embodiments, an isolated antibody or functional fragment thereof is provided, wherein the antibody comprises two or more heavy chain (HC) complementary determining regions (CDRs) selected from (i) a heavy chain LF-hCDR1: GFMFSSYAMS (SEQ ID NO:68); (ii) a heavy chain LF-hCDR2: GISGSGGTTNYADSVKG (SEQ ID NO:69); and (iii) a heavy chain LF-hCDR3: DGVYGRLGGSDY (SEQ ID NO:70), and the antibody or functional fragment thereof can bind specifically to *B. anthracis* lethal factor. In some embodiments, an isolated antibody or functional fragment thereof is provided, wherein the antibody comprises three heavy chain (HC) complementary determining regions (CDRs) consisting of (i) a heavy chain LF-hCDR1: GFMFSSYAMS (SEQ ID NO:68); (ii) a heavy chain LF-hCDR2: GISGSGGTTNYADSVKG (SEQ ID NO:69); and (iii) a heavy chain LF-hCDR3: DGVYGRLGGSDY (SEQ ID NO:70), and the antibody or functional fragment thereof can bind specifically to *B. anthracis* lethal factor. Nucleic acid compositions encoding the foregoing antibody or fragment sequences are further provided.

In some embodiments, an isolated antibody or functional fragment is provided wherein the antibody comprises three light chain (LC) complementary determining regions (CDRs) consisting of: (i) a light chain LF-1CDR1: RASQSVGSSLH (SEQ ID NO:65), (ii) a light chain LF-1CDR2: YASQSFS (SEQ ID NO:66); and (iii) a light chain LF-1CDR3: HQSSSLPLT (SEQ ID NO:67), and three heavy chain complementary determining regions (CDRs) consisting of (i) a heavy chain LF-hCDR1: GFMFSSYAMS (SEQ ID NO:68); (ii) a heavy chain LF-hCDR2: GISGSGGTTNYADSVKG (SEQ ID NO:69); and (iii) a heavy chain LF-hCDR3: DGVYGRLGGSDY (SEQ ID NO:70), and the antibody or functional fragment thereof can bind specifically to *B. anthracis* lethal factor.

In certain embodiments, a LF-1 antibody functional fragment is any one of an Fv, Fab, F(ab)$_2$ or an scFV functional fragment.

Antibody Compositions and Delivery Vehicles and Methods

The invention provides antibody compositions comprising one or more antibodies prepared according to the methods of the invention. An "antibody composition" refers to a composition comprising one or more antibodies or functional fragment(s) thereof and, optionally, any components of the production system that are not removed during the process of purifying the antibody. Thus it will be appreciated that a first antibody composition comprising an antibody or functional fragment thereof prepared by expressing a cDNA isolated using the oligonucleotide primers of the invention in an expression system of choice, e.g., a plant-based expression system, may not be identical to a second antibody composition comprising the same antibody wherein the second antibody composition is prepared using a different expression system. For example, an antibody composition comprising an antibody produced by a hybridoma maintained in tissue culture may contain residual components found in the tissue culture medium, whereas an antibody produced using a plant-based expression system would generally not contain certain of these components. Thus in certain embodiments the antibody compositions of the invention are distinct from other antibody compositions containing the same antibody or antibodies.

In some embodiments one or more antibodies prepared according to the methods of the invention is provided in a pharmaceutical composition suitable for administration to a subject for diagnostic and/or therapeutic purposes, where "therapeutic purposes" are understood to include prophylactic purposes (i.e., administration before any sign or symptom of a disease or condition has occurred) and treatment purposes (i.e., administration after one or more signs or symptoms of a disease or condition has occurred). Antibodies of the invention may, without limitation, be used diagnostically, prophylactically, and/or for treatment of infectious diseases (e.g., bacterial, viral, fungal, or parasitic disease), cancer (which term encompasses carcinomas, sarcomas, lymphoma, leukemia, myelodysplastic syndromes, benign tumors, etc.), inflammatory conditions, disorders characterized by undesirable angiogenesis, transplant rejection, graft vs host disease, etc. Other applications for antibodies of the invention include in vitro immunodepletion of undesired cells such as cancer cells, lymphocytes, etc. The antibodies can also be used to target other agents (e.g., a diagnostic or therapeutic agent) to a site in the body where the antigen recognized by the antibody is expressed.

Suitable preparations, e.g., substantially pure preparations of the antibodies may be combined with pharmaceutically acceptable carriers, diluents, solvents, etc., to produce an appropriate pharmaceutical composition. The invention therefore provides a variety of pharmaceutically acceptable compositions for administration to a subject comprising (i) an antibody; and (ii) a pharmaceutically acceptable carrier, adjuvant, or vehicle. It is to be understood that the pharmaceutical compositions of the invention, when administered to a subject, are preferably administered for a time and in an amount sufficient to treat or prevent the disease or condition for whose treatment or prevention they are administered.

In various embodiments of the invention an effective amount of the pharmaceutical composition is administered to a subject by any suitable route of administration including, but not limited to, intravenous, intramuscular, by inhalation, by catheter, intraocularly, orally, rectally, intradermally, by application to the skin, etc.

Inventive compositions may be formulated for delivery by any available route including, but not limited to parenteral, oral, by inhalation to the lungs, nasal, bronchial, opthalmic, transdermal (topical), transmucosal, rectal, and vaginal routes. The term "parenteral" as used herein includes subcutaneous, intravenous, intramuscular, intra-articular, intrasynovial, intrasternal, intrathecal, intrahepatic, intralesional and intracranial injection or infusion techniques.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Solvents, dispersion media, coatings, antibacterial and antifungal agents, isotonic and absorption delaying agents, and the like, compatible with pharmaceutical administration may be included. Supplementary active compounds, e.g., compounds independently active against the disease or clinical condition to be treated, or compounds that enhance activity of a compound, can also be incorporated into the compositions.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

A pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), phosphate buffered saline (PBS), or Ringer's solution.

Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In all cases, the composition should be sterile, if possible, and should be fluid to the extent that easy syringability exists.

Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of injectable compositions can be brought about by including in the composition an agent which delays absorption, for example, aluminum monostearate and gelatin. Prolonged absorption of oral compositions can be achieved by various means including encapsulation.

Sterile injectable solutions can be prepared by incorporating the active compound in the required amount in an appropriate solvent with one or a combination of ingredients enumerated above, as required, followed by filtered sterilization. Preferably solutions for injection are free of endotoxin. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive compositions are preferably delivered in the form of an aerosol spray from a pressured container or dispenser which contains a suitable propellant, e.g., a gas such as carbon dioxide, or a nebulizer. Liquid or dry aerosol (e.g., dry powders, large porous particles, etc.) can be used. The present invention also contemplates delivery of compositions using a nasal spray.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2☐octyldodecanol, benzyl alcohol and water.

For local delivery to the eye, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the antibodies are formulated into ointments, salves, gels, or creams as generally known in the art.

The antibody compositions can also be prepared in the form of suppositories (e.g., with conventional suppository bases such as cocoa butter and other glycerides) or retention enemas for rectal delivery.

In addition to the agents described above, in certain embodiments of the invention, the antibody compositions are prepared with carriers that will protect the antibodies against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polyethers, and polylactic acid. Methods for preparation of such formulations will be apparent to those skilled in the art. Certain of the materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811 and other references listed herein. Liposomes, including targeted liposomes (e.g., antibody targeted liposomes) and pegylated liposomes have been described (Hansen C B, et al., *Biochim Biophys Acta.* 1239(2):133-44, 1995; Torchilin V P, et al., *Biochim Biophys Acta,* 1511(2): 397-411, 2001; Ishida T, et al., *FEBS Lett.* 460(1):129-33, 1999). One of ordinary skill in the art will appreciate that the materials and methods selected for preparation of a controlled release formulation, implant, etc., should be such as to retain activity of the antibody. For example, it may be desirable to avoid excessive heating of polypeptides such as antibodies, which could lead to denaturation and loss of activity.

It is typically advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of antibody calculated to produce the desired therapeutic effect in association with the required pharmaceutical carrier.

Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions which exhibit high therapeutic indices are preferred. While compositions that exhibit toxic side effects can be used, care should be taken to design a delivery system that targets such compositions to the site of affected tissue in order to minimize potential damage to uninfected cells and, thereby, reduce side effects.

The data obtained from cell culture assays and animal studies can be used in formulating a range of dosage for use in humans. The dosage lies preferably within a range of circulating concentrations that include the $ED_{50}$ with little or no toxicity. The dosage can vary within this range depending upon the dosage form employed and the route of administration utilized. For any antibody or other compound used in the method of the invention, the therapeutically effective dose can be estimated initially from cell culture assays. A dose can be formulated in animal models to achieve a circulating plasma concentration range that includes the $ED_{50}$ as determined in cell culture. Such information can be used to more accurately determine useful doses in humans. Levels in plasma can be measured, for example, by high performance liquid chromatography.

A therapeutically effective amount of a pharmaceutical composition typically ranges from about 0.001 to 100 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The pharmaceutical composition can be administered at various intervals and over different periods of time as required, e.g., multiple times per day, daily, every other day, once a week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Generally, treatment of a subject with an inventive composition can include a single treatment or, in many cases, can include a series of treatments. It will be appreciated that a range of different dosage combinations (i.e., doses of two or more antibodies or one or more antibodies and one or more additional active agents) can be used.

Exemplary doses include milligram or microgram amounts of the antibodies per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram.) For local administration (e.g., intranasal), doses much smaller than these may be used. It is furthermore understood that appropriate doses depend upon the potency of the agent, and may optionally be tailored to the particular recipient, for example, through administration of increasing doses until a preselected desired response is achieved. It is understood that the specific dose level for any particular subject may depend upon a variety of factors including the activity of the specific compound employed, the age, body weight, general health, gender, and diet of the subject, the time of administration, the route of administration, the rate of excretion, any drug combination, and the degree of expression or activity to be modulated.

The invention further provides pharmaceutical compositions comprising two or more antibodies of the invention and, optionally, one or more additional active agents.

EXAMPLES

The below Examples describe cDNAs were cloned from human hybridoma cell lines which produce antibodies which specifically bind *B. anthracis* PA or LF protein. cDNAs for the human heavy and light chain of monoclonal antibody specifically recognizing PA (designated herein PA) or LF (designated herein LF) were isolated from hybridoma cell lines which were generated from cells isolated from a human patient immunized with a licensed anthrax vaccine.

Example 1

Isolation of cDNAs that Encode Human Monoclonal Antibodies from Hybridomas

This example describes use of certain of the oligonucleotide primers listed in Table 1 to isolate cDNAs encoding human monoclonal antibodies. All kits were used according to the manufacturer's directions.

RNA-Purification from Hybridoma Cell Lines.

Total RNA was purified from $10^5$ cells of any given hybridoma cell line using the RNeasy Mini Kit (Qiagen). The RNA was eluted in 50 µl water (no yield was calculated) and 5 µl was used in each RT-PCR reaction.

Reverse Transcription-PCR.

The primers used for RT-PCR are listed in Table 1. RT-PCR was performed with Superscript One-Step RT-PCR with Platinum Taq DNA polymerase (Invitrogen). To efficiently target all possible variable regions in any given heavy or light chain sequence a combination of primers were used for each RT-PCR reaction and several RT-PCR reactions were performed simultaneously for amplification of each antibody gene.

For heavy chains, 2 µM each of the primers VG1+7 short, VG2 short and VG3 short were combined with 2 µM of the constant gamma short (CG short) primer in one reaction and 2 µM each of the primers VG4-short, VG5-short and VG6-short were combined with 2 µM of the constant gamma short (CG-short) primer in a second reaction. Any product was then purified using Qiaex II (Qiagen) and, if the product came from the first initial reaction, re-amplified with 2 µM each of the primers VG1, VG2, and VG3 in combinations with 2 µM of primer CG, or, if the product came from the second RT-PCR reaction, re-amplified with 2 µM each of the primers VG4, VG5, and VG6 in combinations with 2 µM of primer CG using Platinum PCR SuperMix High Fidelity (Invitrogen) to introduce different 5' and 3' Sfi I restriction sites.

For light chains, the RT-PCR product yield was always sufficient for immediate subcloning of the product, thus eliminating the need for an initial RT-PCR reaction with short primers. Instead 2 µM each of three variable region primers were combined with 2 µM of the constant region primer (Table 1), resulting in three separate reactions for lambda and two separate reactions for kappa light chains. Specifically, the reactions contained 2 or 3 variable primers, as follows:

CK+VK1, 2+1.8 and 3
CK+VK 4 and 5
CL+VL1, 2 and 3
CL+VL4, 5 and 6+9
CL+VL7 and 10+8

It will be appreciated that other combinations could have been used.

PCR cycling conditions were adapted from Krebber, A., Bornhauser, S., Burmester, J., Honegger, A., Willuda, J., Bosshard, H. R., and Pluckthun, A. (1997). Reliable cloning of functional antibody variable domains from hybridomas and spleen cell repertoires employing a reengineered phage display system. *J Immunol Methods* 201, 35-55. For RT-PCR the cycling conditions were as follows: 30 min at 45° C., 2 min at 94° C., seven cycles of: 1 min at 94° C., 30 sec at 63° C., 50 sec at 58° C., 3 min at 72° C., and 33 cycles of: 1 min at 94° C., 1 min at 63° C., and 3 min at 72° C., followed by 7 min at 72° C. For regular PCR (not RT-PCR) the initial steps of 30 min at 45° C. and 2 min at 94° C. were omitted.

The amplification products were cloned into the binary vector pBISfi, whose construction is described in Example 2.

Example 2

Construction of Vector pBISfi

This example describes modification of the binary vector pBI121 to facilitate its use for expression of antibodies in plants. First, the internal Sfi I site at 11031 bp of vector pBI121 was mutagenized as follows: the vector was digested with Sfi I and the resulting single stranded overhangs were filled in using Klenow and the resulting blunt ends were re-ligated. To create a 5' unique Sfi I site the oligonucleotides BamSfi 1 (5'-GATCCGGCCCAGCCGGCCG-3'; SEQ ID NO: 53) and BamSfi 2 (5'-GATCCGGCCGGCTGGGCCG-3'; SEQ ID NO: 54) were annealed to each other and ligated into the BamH I site of the vector pBI121 (lacking the internal Sfi I site). Similarly, annealing oligonucleotides SacSfi 1 (5'-GCCTCGGGGGCCGAGCT-3'; SEQ ID NO: 55) and SacSfi 2 (5'-GCCCCCGAGGCCGAGCT-3'; SEQ ID NO: 56) and ligating into the Sac I site of pBI121 (lacking the internal Sfi I site) created a 3' unique Sfi I site.

Example 3

Mutagenesis of cDNA Encoding PA Antibody Heavy Chain

The cDNA that encodes the PA gamma chain was mutagenized using Invitrogen's GeneTailor kit according to the manufacturer's recommendations so as to alter the N-glycosylation site at position 318 of the PA gamma chain. The following mutant primer was used: 5'-ccgcgggaggagcagtac-CAAagcacgtaccgt-3' (SEQ ID NO: 57). The reverse primer was: gtactgctcctcccgcggctttgtcttggca (SEQ ID NO: 58) As a result of the mutagenesis, the AAC codon was replaced by a CAA codon, resulting in an Asn->Gln alteration.

Example 4

Production of Glycosylated and Nonglycosylated PA Antibody in Plants

Glycosylated and non-glycosylated PA antibody (PA and PANG, respectively) were purified from the leaves of *Nicotiana benthamiana* plants after agro-infiltration with a 1:1 mixture of Agrobacterial cultures carrying light or heavy chain cDNAs under the 35S promoter in pBISfil. The antibodies were purified using protein A- and T-gel chromatography and compared using SDS-PAGE. FIG. 1 shows an image of the gel, which clearly demonstrates a difference in the electrophoretic mobility of PANG heavy chains due to the lack of glycosylation, i.e., the PANG heavy chain migrates faster than the PA heavy chain since it is lighter. Western blot and ELISA analysis confirmed the specific binding activity of PA, PANG and LF antibodies for PA and LF, respectively, indicating that production in plants did not impair the specificity of antibody binding.

Example 5

Half-Life Study of Anti-PA and Anti-LF Human Monoclonal Antibodies in Rats

Male Fischer rats were injected intraperitoneally with 50 μg of either plant produced PA, plant produced PANG, or plant produced LF. Serum samples were taken pre-injection, as well as at 2 hrs, and at 1, 2, 3, 4, 5, 10, 15, and 20 days post-injection. Serum was analyzed with either PA- or LF-specific binding ELISA. Plant produced PA and PANG showed similar half-lifes, while LF antibodies had somewhat lower half life as compared to both plant produced PA antibodies.

Example 6

Animal Protection Studies

The ability of plant produced PA to protect A/J mice against challenge with spores of the Sterne strain of *B. anthracis* was determined according to the method of Beedham and colleagues. A group of five mice were given 180 μg of plant produced PA mAb by intraperitoneal route in PBS. Control mice received PBS. 2.5 hours after passive immunization, animals received spores of *B. anthracis* at a dose of $1\times10^4$ spores in 0.1 mL of PBS (approximately 30 median lethal dose). Following challend, animals were monitored daily for 14 days for evidence of morbidity or mortality. Animals receiving plant produced mAb did not develop disease symptoms, remained healthy, and survived the challenge, while all the control animals developed disease and died within 3 days post-challenge.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. Furthermore, it is to be understood that the invention encompasses all variations, combinations, and permutations in which one or more limitations, elements, clauses, descriptive terms, etc., from one or more of the listed claims is introduced into another claim. In particular, any claim that is dependent on another claim can be modified to include one or more limitations found in any other claim that is dependent on the same base claim. In addition, it is to be understood that any particular embodiment of the present invention that falls within the prior art may be explicitly excluded from the claims. Since such embodiments are deemed to be known to one of ordinary skill in the art, they may be excluded even if not set forth explicitly herein. For example, any specific oligonucleotide, cDNA, nucleic acid, or antibody, can be excluded from the claims.

---

We claim:

1. A method of isolating a nucleic acid that encodes an antibody heavy chain comprising the sequence set forth in SEQ ID NO:48 or SEQ ID NO:52, comprising amplifying said nucleic acid from a cell or cell line that produces the antibody heavy chain using a primer mix of comprising:
   SEQ ID NOS: 2, 13, 14, and 15,
   SEQ ID NOS: 2, 16, 17, and 18,
   SEQ ID NOS: 1, 7, 8, and 9, or
   SEQ ID NOS: 1, 10, 11, and 12.

2. The method of claim 1, comprising using a primer comprising the sequence set forth in SEQ ID NO: 2 in combination with primers comprising the sequences set forth in SEQ ID NOS: 13, 14, and 15, or SEQ ID NOS: 16, 17, and 18.

3. The method of claim 1, comprising using a primer comprising the sequence set forth in SEQ ID NO: 1 in combination with primers comprising the sequences set forth in SEQ ID NOS: 7, 8, and 9, or SEQ ID NOS: 10, 11, and 12.

4. The method of claim 1, comprising using a primer consisting of the sequence set forth in SEQ ID NO: 2 in combination with primers consisting of the sequences set forth in SEQ ID NOS: 13, 14, and 15, or SEQ ID NOS: 16, 17, and 18.

5. The method of claim 1, comprising using a primer consisting of the sequence set forth in SEQ ID NO: 1 in combination with primers consisting of the sequences set forth in SEQ ID NOS: 7, 8, and 9, or SEQ ID NOS: 10, 11, and 12.

\* \* \* \* \*